(12) United States Patent
Adachi

(10) Patent No.: US 7,838,610 B2
(45) Date of Patent: Nov. 23, 2010

(54) ION-SENSITIVE SUPER-ABSORBENT POLYMER

(75) Inventor: Yoshifumi Adachi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 181 days.

(21) Appl. No.: 11/525,098

(22) Filed: Sep. 22, 2006

(65) Prior Publication Data
US 2007/0078248 A1 Apr. 5, 2007

(30) Foreign Application Priority Data
Sep. 30, 2005 (JP) ............................ 2005-288437

(51) Int. Cl.
*C08F 20/06* (2006.01)
(52) U.S. Cl. ..................... 526/317.1; 526/319; 526/328
(58) Field of Classification Search .............. 526/317.1, 526/319, 328; 523/111
See application file for complete search history.

(56) References Cited

U.S. PATENT DOCUMENTS

| | | | |
|---|---|---|---|
| 3,915,921 A * | 10/1975 | Schlatzer, Jr. .......... 526/238.23 |
| 4,062,817 A * | 12/1977 | Westerman .............. 525/330.2 |
| 4,066,583 A | 1/1978 | Spaulding |
| 4,167,464 A | 9/1979 | George |
| 4,526,937 A | 7/1985 | Hsu |
| 4,535,098 A | 8/1985 | Evani et al. |
| 5,051,259 A | 9/1991 | Olsen et al. |
| 5,312,883 A | 5/1994 | Komatsu et al. |
| 5,317,063 A | 5/1994 | Komatsu et al. |
| 5,466,731 A | 11/1995 | Akers et al. |
| 5,582,786 A | 12/1996 | Brunskill et al. |
| 5,601,542 A | 2/1997 | Melius et al. |
| 5,631,317 A | 5/1997 | Komatsu et al. |
| 5,669,894 A | 9/1997 | Goldman et al. |
| 5,830,201 A * | 11/1998 | George et al. ............... 604/364 |
| 6,071,976 A | 6/2000 | Dairoku et al. |
| 6,187,872 B1 | 2/2001 | Yanase et al. |
| 6,228,930 B1 | 5/2001 | Dairoku et al. |

(Continued)

FOREIGN PATENT DOCUMENTS

EP 0 496 067 A2 7/1992

(Continued)

OTHER PUBLICATIONS

Mark Elliott (http://www.functionalpolymers.basf.com/portal/streamer?fid=291074).*

(Continued)

*Primary Examiner*—David Wu
*Assistant Examiner*—Vu A Nguyen
(74) *Attorney, Agent, or Firm*—Buchanan Ingersoll & Rooney PC

(57) ABSTRACT

The present invention is to provide a super-absorbent resin which can be used to design an absorbing core or absorbing goods capable of being flown into a flushing toilet. The present invention relates to a super-absorbent resin having as a main component thereof a repeating unit having an ionic dissociation group in its main or side chain, wherein said resin has absorption capacity without load to saline solution (CRCs) for 4 hours of not smaller than 10 g/g, and solubility in ion-exchanged water of not lower than 50% by weight.

17 Claims, 1 Drawing Sheet

U.S. PATENT DOCUMENTS

Figure 1:
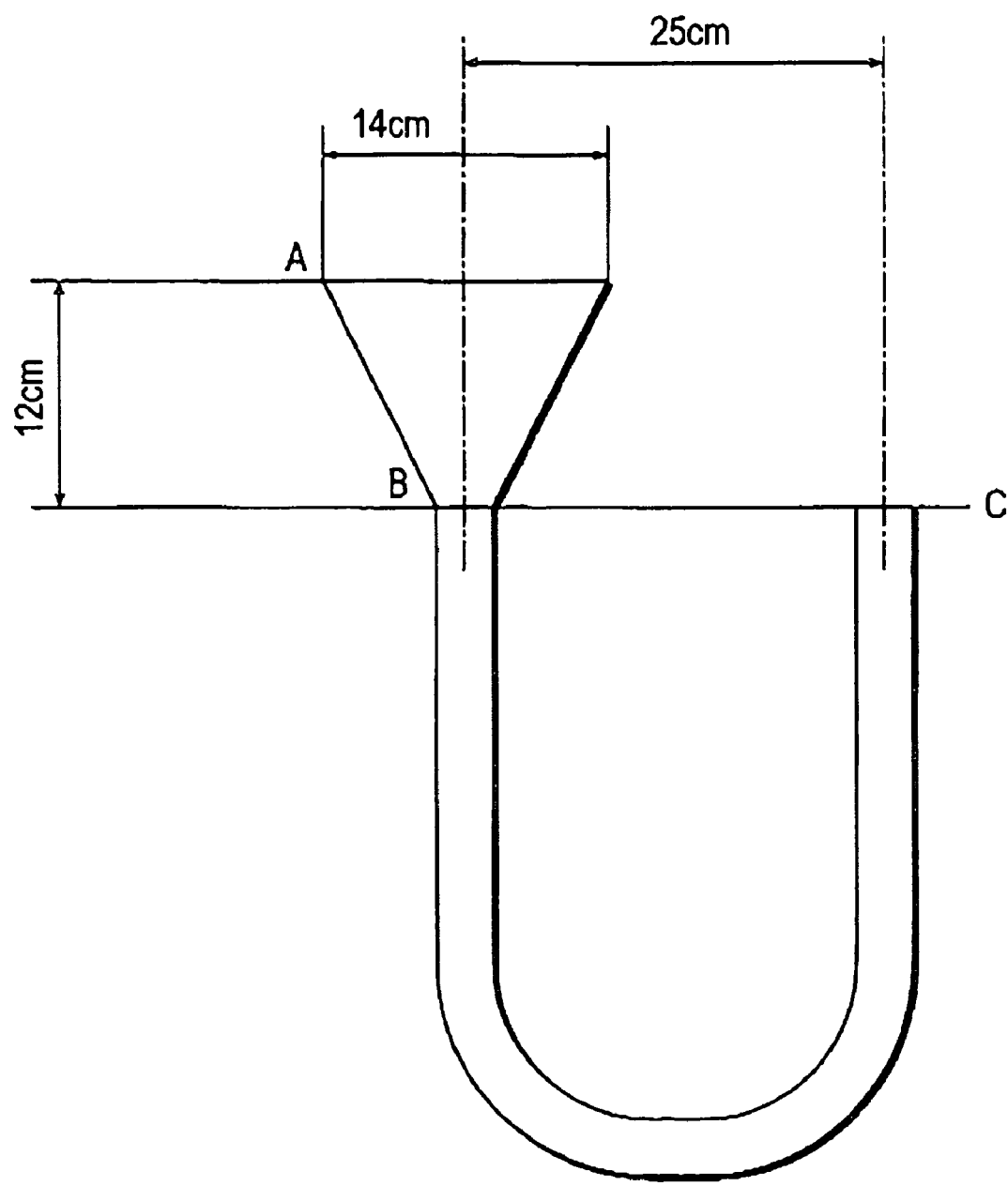

| | | | |
|---|---|---|---|
| 6,254,990 | B1 | 7/2001 | Ishizaki et al. |
| 6,291,372 | B1 | 9/2001 | Mumick et al. |
| 6,423,804 | B1 | 7/2002 | Chang et al. |
| 6,537,663 | B1 | 3/2003 | Chang et al. |
| 6,548,592 | B1 | 4/2003 | Lang et al. |
| 6,555,619 | B1 | 4/2003 | Kennedy et al. |
| 6,599,848 | B1 | 7/2003 | Chen et al. |
| 6,683,143 | B1 | 1/2004 | Mumick et al. |
| 2005/0049379 | A1* | 3/2005 | Adachi et al. ............... 526/319 |
| 2005/0118423 | A1 | 6/2005 | Adachi et al. |
| 2006/0189738 | A1 | 8/2006 | Ueda et al. |

FOREIGN PATENT DOCUMENTS

| | | | |
|---|---|---|---|
| EP | 0 601 529 A1 | 6/1994 |
| EP | 0 942 014 A2 | 9/1999 |
| EP | 1 178 059 A2 | 2/2002 |
| EP | 1 191 051 A2 | 3/2002 |
| JP | 52-123490 | 10/1978 |
| JP | 53-141357 | 12/1978 |
| JP | 60-71623 A | 4/1985 |
| JP | 63-139906 A | 6/1988 |
| JP | 2-2969 A | 1/1990 |
| JP | 2-2969 B2 | 1/1990 |
| JP | 7-292040 A | 11/1995 |
| JP | 3148307 B2 | 3/2001 |
| JP | 3162969 B2 | 5/2001 |
| WO | 82/00147 A1 | 1/1982 |
| WO | 93/24684 A1 | 12/1993 |
| WO | 94/04724 A1 | 3/1994 |
| WO | 99/52482 A1 | 10/1999 |
| WO | 2004/069936 A1 | 8/2004 |
| WO | WO 2004/069404 A1 * | 8/2004 |
| WO | 2005-010102 A1 | 2/2005 |

OTHER PUBLICATIONS

Mark Elliott @ www.functionalpolymers.basf.com/portal/streamer?fid=286903 (2004).*
Orzeszyna et al., Int. Agrophysics vol. 20, 2006, pp. 201-206.*
European Search Report dated Feb. 12, 2007.
Office Action issued Mar. 31, 2010 in corresponding European Patent Application No. 06121577.8.

* cited by examiner

ION-SENSITIVE SUPER-ABSORBENT POLYMER

BACKGROUND OF THE INVENTION

1. Field of the Invention

The present invention relates to a super-absorbent resin. In particular, it relates to a super-absorbent resin used in such as a disposable diaper or a sanitary napkin, characterized in absorbing body fluid but being soluble in water.

2. Description of the Related Art

At present, in hygienic goods such as a disposable diaper or a sanitary napkin, so-called an incontinence pad, as component material thereof, a super-absorbent resin or hydrophilic fiber such as pulp has been widely used aiming at absorbing body fluid. As the super-absorbent resin, for example, partially neutralized and crosslinked polyacrylic acid, a hydrolyzed or crosslinked starch-acrylonitrile graft polymer, a neutralized or crosslinked starch-acrylic acid graft polymer, a saponified or crosslinked vinyl acetate-acrylate ester copolymer, a hydrolyzed or crosslinked acrylonitrile copolymer, or a crosslinked acrylamide copolymer and a crosslinked polymer of a cationic monomer have been used as a main raw material.

As a method for improving performance of the conventional super-absorbent resin, methods for attaining high absorption capacity to aqueous fluid such as body fluid excellent absorption rate, and high fluid permeability have been proposed in U.S. Pat. No. 5,601,542 and U.S. Pat. No. 5,669,894. However, super-absorbent resins which have been proposed up to now, because they are prepared in a firmly cross-linked form by using a cross-linking agent and the like, not only exhibit high absorption to an aqueous solution containing a salt such as body fluid, but also exhibit high absorption capacity to water (including ion-exchanged water, distilled water, and tap water), and had a problem that a drainage pipe could be clogged when they are flown into a flushing toilet and the like. Due to this problem, the conventional super-absorbent resins have actually been necessary to be disposed by incineration, landfill, and the like, which necessitates a large amount of energy.

In addition, according to a well-known technology, so-called an ion-sensitive film or binder has been proposed, solubility of which is varied depending on ion concentrations (see U.S. Pat. No. 5,631,317, U.S. Pat. No. 5,317,063, U.S. Pat. No. 5,312,883, U.S. Pat. No. 4,535,098, U.S. Pat. No. 6,291,372, U.S. Pat. No. 6,423,804, U.S. Pat. No. 6,683,143, U.S. Pat. No. 6,537,663 and JP-A63-139906, for example).

However, the technologies disclosed in these publications have such a problem as of low absorption performance to body fluid, and low solubility in water, and have failed to provide such an absorbent agent of body fluid that can be flushed down a toilet basin. Further, in the use thereof, a method for producing an absorbing core with high strength has been adopted, which comprises spraying a polymer solution as a binder on an absorbing core web formed, and drying. There, however, has a problem that an absorbing core becomes hard and has decreased acquisition rate of fluid into an absorbing core, when a large quantity of the polymer was introduced in an absorbing core. Accordingly, such a conventional polymer could not be used except for as a small amount of an additive like a binder, and water-absorbing performance has not been pursued to the polymer.

SUMMARY OF THE INVENTION

In the above circumstances, it is an object of the present invention to provide a super-absorbent resin capable of designing an absorbing core or absorbing goods, which can be flushed directly down a toilet basin and the like, which has been attained by a conventional super-absorbent resin with much difficulties.

The present inventors have extensively studied a way to solve the problems, find that a conventional super-absorbent resin can not be flushed down a toilet basin and the like due to its high swelling properties to water. The conventional super-absorbent resin, as described above has an extremely strong cross-linked form, is hardly soluble in water and, because it was designed to be a chemically cross-linked substance of acrylate and the like, and little dissolves in water and exhibits several hundreds times as of high swelling properties relative to water (including ion-exchanged water, distilled water, and tap water). However, performance required to a disposable diaper or a sanitary napkin is high absorption capacity of excretory fluid from a body. All of excretory fluid from a body is an electrolyte solution containing a salts with a concentration of not less than about 0.4% by weight, and the requirement can be satisfied by only securing absorption capacity to these electrolyte solutions. In a super-absorbent resin according to conventional technology, chemical cross-linking has been introduced to manifest absorption to an electrolyte solution, resulting in secondary exhibition of high absorption capacity also to water. In particular, in the case when a polymer used in a super-absorbent resin has a dissociating ionic group, absorption capacity of water without load increases to 200 g/g to 500 g/g, although that of an aqueous electrolyte solution such as saline solution is only 20 g/g to 50 g/g. They have found that decrease in electrolyte concentration in a solution to be absorbed significantly increases absorption capacity of a super-absorbent resin, which induces clogging of a drainage pipe, when a super-absorbent resin is flushed down a toilet basin. Of course, when a polymer used in a super-absorbent resin has no dissociating ionic groups, although change in absorption capacity depending on an electrolyte concentration of a solution is little, absorption capacity or absorption rate itself, which is key property, significantly is lowered, and thus such a polymer can not be advantageously applied to a disposable diaper or a sanitary napkin.

In this circumstance, the present inventors have found that a super-absorbent resin having as a main component thereof a repeating unit having an ionic dissociation group in its main or side chain can manifest specific solubility in water while keeping absorption capacity to saline solution of not lower than a specific level, and thus such a resin can be used to design a disposable diaper or a sanitary napkin which can be flushed down a toilet basin and the like. Based on this knowledge, the present invention has been completed.

Specifically, a super-absorbent resin of the present invention is a super-absorbent resin having as a main component thereof a repeating unit having an ionic dissociation group in its main or side chain, wherein said resin has absorption capacity without load to saline solution (CRCs) for 4 hours of not smaller than 10 g/g, and solubility in ion-exchanged water of not lower than 50% by weight.

A super-absorbent resin of the present invention has such merits as in manifesting absorption performance to body fluid to a similar level to that of conventional one and thus excelling in use feeling, when used in a disposable diaper or a sanitary napkin, and can provide convenience of permitting direct flushing down a toilet basin and the like.

The above and other objects, features and advantages of the present invention will become clear from the following description of the preferred embodiments.

BRIEF DESCRIPTION OF DRAWING(S)

FIG. 1 is a schematic diagram of a device used in the blockage test in simulated pipe.

DESCRIPTION OF THE PREFERRED EMBODIMENT(S)

The present invention relates to a super-absorbent resin having as a main component thereof a repeating unit having an ionic dissociation group in its main or side chain, wherein said resin has absorption capacity without load to saline solution (CRCs) for 4 hours of not smaller than 10 g/g, and solubility in ion-exchanged water of not lower than 50% by weight. As used herein, the super-absorbent resin of the present invention is occasionally referred to as "ion-sensitive super-absorbent resin".

A raw material used in a super-absorbent resin of the present invention, reaction conditions, and the like will be described below. In this connection, "saline solution", as used herein, is referred to as a 0.90% by weight sodium chloride aqueous solution, "water", as used herein, is referred to as a solution with a low electrolyte concentration (which approximately means an electrolyte concentration of less than 0.1% by weight, more preferably less than 0.05% by weight), including tap water, ion-exchanged water, and distilled water, and air temperature thereof to be used is 25±2° C. and the liquid temperature is 21±2° C., unless otherwise specified.

(1) Mechanism of an Ion-Sensitive Super-Absorbent Resin

A super-absorbent resin of the present invention is a compound having high absorbency to saline solution, and specifically, is a compound absorption capacity without load to saline solution of 0.90% by weight for 4 hours of not smaller than 10 g/g. In this connection, a measurement method there for is specified in Examples below. A super-absorbent resin of the present invention may optionally contain a trace component such as a small amount of an additive and water. In this case, a ratio of water or small amount of additive is in the range of 0 to 30% by weight, preferably 0 to 20% by weight, and further preferably not less than 0% by weight and less than 10% by weight, based on total weight of the super-absorbent resin. As a trace component, usually water may be mainly used, and further additive which will be described later may be used. A super-absorbent resin of the present invention is used to absorb and immobilize a solution containing an electrolyte. An aqueous solution containing an electrolyte is an aqueous solution containing an electrolyte of not less than 0.4% by weight, including urine, blood, excrement, body fluid, waste fluid containing blood, sea water and the like. Preferably, the super-absorbent resin is used to absorb and immobilize urine, in particular human urine.

Although a mechanism of a super-absorbent resin of the present invention to express ion-sensitivity is not certain, it is considered as follows. First, it is considered that a super-absorbent resin is required to essentially have, as a main component, a repeating unit having an ionic dissociation group in its main or side chain.

As above, by using a super-absorbent resin having as a main component a repeating unit having an ionic dissociation group in its main or side chain, osmotic pressure derived from the polymer would increase. Therefore, not only large absorption capacity to saline solution can be designed but also osmotic pressure thereof becomes maximal when contacted with water. Namely, such design can make osmotic pressure varied depending on a salt concentration of fluid to be contacted.

In addition, in one embodiment, a super-absorbent resin having a hydrocarbon group of 4 or more carbon atoms at the side chain is considered preferable.

When a hydrocarbon group is present as above, aggregation of the hydrocarbon group (so-called salting out) would be promoted against osmotic pressure derived from the ionic dissociation group in the case of a high salt concentration of a solution to be absorbed. Further, the aggregation would provide a cross-linking point to create water-swelling properties. On the other hand, when a salt concentration of a solution to be absorbed is low, since osmotic pressure derived from the ionic dissociation group would overcome aggregation of the hydrocarbon group, the super-absorbent resin is considered to show solubility.

In another embodiment, when a polymer having as a main component a repeating unit having an ionic dissociation group in its main or side chain is in a particulate or fibrous form, the formation of a membrane by introducing chemical cross-linking (surface cross-linking treatment) selectively at vicinity of the surface thereof permits swelling property to saline solution and solubility in water to be simultaneously attained. Therefore, in the present invention, it is considered to be preferable that chemical cross-linking (surface cross-linking treatment) may be introduced at vicinity of the surface of a particle, fiber, and the like, but a firm network is not formed by uniform chemical cross-linking in the particle or fiber.

Specifically, in the present invention, it has been found that, by suitably combining such factors, i.e., osmotic pressure derived from an ionic dissociation group, aggregation force derived from a hydrocarbon group or chemical cross-linking only at the vicinity of the surface, and salt concentration of a solution to be absorbed, and at the same time, by adjusting absorption characteristics of a super-absorbent resin so that absorption capacity without load to saline solution (CRCs) for 4 hours is not smaller than 10 g/g and solubility in ion-exchanged water is not lower than 50% by weight, absorbing goods using the super-absorbent resin can be designed so as to be flushed down a toilet basin after use. The present invention has a feature in finding a fact that when a super-absorbent resin satisfies such specific parameters, clogging of a drainage pipe having many bends never occurs, even when absorbing goods or an absorbing core after use are flushed with water into it. In particular, in a drainage pipe having a plurality of bends, a super-absorbent resin is easily accumulated at such bends, and in the case of a conventional super-absorbent resin, the super-absorbent resin swells with water and blocks a drainage pipe at the bends. On the other hand, when a super-absorbent resin satisfies the specific parameter range according to the present invention, the blocking can be eliminated.

"An ion-sensitive" as used herein is applied to characteristics satisfying the parameters based on mechanism described above. An ion-sensitive super-absorbent resin of the present invention can be adopted, by satisfying the parameters, in various applications to be used as a super-absorbent resin which can be flushed into a drainage pipe after use. As a rough guideline for practical applicability, it means that a super-absorbent resin shows high degree of swelling to an aqueous solution containing a salt (for example, such as NaCl, KCl, $CaCl_2$, and $MgCl_2$) with a concentration of not lower than 0.4% by weight, and also solubility not only in ion-exchange water but also in usual water.

A method for introducing a hydrocarbon group in the side chain into a repeating unit, having an ionic dissociation group in the main or side chain as a main component may be such a method for introducing a hydrocarbon side chain into a polymer having as a main component a repeating unit having an ionic dissociation group in the main or side chain; or a method for obtaining a polymer by copolymerization of a monomer having an ionic dissociation group in the main or side chain, and a monomer having a hydrocarbon group in the side chain.

"An ionic dissociating group" as used herein represents a functional group which is dissociated in water to generate ionic dissociation. Such an ionic dissociating group includes a functional group showing acidity by dissociation in an aqueous solution like a carboxyl group, a sulfonic acid group, and a phosphoric group; a functional group showing basicity by dissociation in an aqueous solution like an amino group; and the salts thereof, for example. As the salt, alkali metal salts like lithium salt, sodium salt, and potassium salt; alkaline earth metal salts like magnesium salt, strontium salt, and barium salt; and ammonium salt can be included in the case of carboxyl group, sulfonic acid group and phosphoric acid group. Among these groups, lithium salt, sodium salt, and potassium salt, and ammonium salt are preferable. In view of performance, easiness of industrial availability and safety of the resultant super-absorbent resin, sodium salt and potassium salt are more preferable. In the case of an amino group, hydrochloride salt, sulfate salt, carboxylate salt, and phosphate salt and the like can be included. The super-absorbent resin of this invention may be contain one ionic dissociating group or two or more ionic dissociating groups.

"A hydrocarbon group with carbon atoms of not lower than 4" as used herein is a hydrocarbon group composed of carbon and hydrogen and having a sequence chain of 4 or more carbon atoms. In addition, the structure thereof may be any of straight chain, branched chain or cyclic chain, and may be saturated or unsaturated. Length of a hydrocarbon group is not less than 4 and not more than 50 carbon atoms. In view of aggregation performance to saline solution, more preferably is not less than 8 and not more than 50, further more preferably is not less than 10 and not more than 50, and particularly preferably is not less than 12 and not more than 50. In particular, as for a side chain of hydrocarbon group, longer chain is more preferable, because the amount of the hydrocarbon group to be introduced is lowered, ratio of an acid group or salt thereof which can be used is increased and absorption performance can be enhanced. However, length of the hydrocarbon group over 50 is not preferable because handling in polymer synthesis becomes poor.

As typical examples of the hydrocarbon group with carbon atoms of not lower than 4, straight or branched chain saturated alkyls such as butyl, isobutyl, sec-butyl, tert-butyl, pentyl, isopentyl, tert-pentyl, neopentyl, hexyl, isohexyl, heptyl, octyl, nonyl, decyl, undecyl, dodecyl, 2-ethylhexyl, tridecyl, tetradecyl, pentadecyl, hexadecyl, heptadecyl, octadecyl, nonadecyl, eicosyl, heneicosyl, docosyl and the like; cyclic saturated alkyls such as cyclobutyl, cyclopentyl, cyclohexyl, cycloheptyl, cyclooctyl and the like; straight or branched chain unsaturated alkenyls such as butenyl, isobutenyl, sec-butenyl, tert-butenyl, pentenyl, isopentenyl, tert-pentenyl, neopentenyl, hexenyl, isohexenyl, heptenyl, octenyl, nonylenyl, decenyl, undecylenyl, dodecylenyl, 2-ethylhexenyl, tridecylenyl, tetradecylenyl, pentadecylenyl, hexadecylenyl, heptadecylenyl, octadecylenyl, nonadecylenyl, eicosylenyl, heneicosylenyl, docosylenyl and the like; cyclic unsaturated alkenyls such as cyclohexenyl, cyclooctenyl, cyclododecenyl and the like can be cited. Among these hydrocarbon groups, dodecyl, octadecyl, hexadecyl, and tetradecyl are preferable, and dodecyl, octadecyl are more preferable. In particular, when an unsaturated hydrocarbon unit such as an undecylenyl group is used, effects such as antibacterial properties can further be furnished.

In addition, the super-absorbent resin of the present invention contains a hydrocarbon group with carbon atoms of not lower than 4 at the side chain. In this case, the super-absorbent resin of the present invention may contain another side chain, in addition to or in place of the hydrocarbon group with carbon atoms of not lower than 4. As the another side chain, though not limited thereto, polyoxyethylene group, and polyoxypropylene group may also be contained at the side chain.

(2) Method for Producing an Ion-Sensitive Super-Absorbent Resin

A method for producing an ion-sensitive super-absorbent resin of the present invention is not especially limited as long as it satisfies property specified in the present invention. When a super-absorbent resin of the present invention has an ionic dissociation group in its main or side chain and also has a hydrocarbon group with carbon atoms of not lower than 4 at its side chain, for example, the ion-sensitive super-absorbent resin can be obtained by the following "a production method 1" to "a production method 4", for example.

<Production Method 1>

A method for obtaining an ion-sensitive super-absorbent resin which comprises copolymerizing a monomer having an ionic dissociation group in the main or side chain optionally with a monomer having a hydrocarbon group with carbon atoms of not lower than 4 in the side chain, in water or an organic solvent or a mixed solution thereof, and subjecting the resultant copolymer to drying, crushing, and optionally surface cross-linking.

<Production Method 2>

A method for obtaining an ion-sensitive super-absorbent resin which comprises reacting a compound having both a functional group capable of reacting with an acid group or a basic group and a hydrocarbon group with carbon atoms of not lower than 4 with a polymer having as a main component a repeating unit having an ionic dissociation group in its side or main chain, in water or an organic solvent or a mixed solution thereof, and further subjecting to drying, crushing, and optionally surface cross-linking treatment.

<Production Method 3>

A method for obtaining an ion-sensitive super-absorbent resin which comprises copolymerizing a monomer having an ionic dissociation group in the main or side chain optionally with a monomer having a hydrocarbon group with carbon atoms of not lower than 4 in the side chain, in water or an organic solvent or a mixed solution thereof, in the presence of a chain transfer agent, and further subjecting to drying, crushing, and optionally surface cross-linking.

<Production Method 4>

A method for obtaining an ion-sensitive super-absorbent resin which comprises copolymerizing a monomer having an ionic dissociation group in the main or side chain optionally with a monomer having a hydrocarbon group with carbon atoms of not lower than 4 in the side chain, in water or an organic solvent or a mixed solution thereof, in the presence of a surfactant, and further subjecting to drying, crushing, and optionally surface cross-linking.

The methods for producing an ion-sensitive super-absorbent resin ("production methods 1 to 4") and further a super-absorbent resin of the present invention will be explained successively.

(3) Unsaturated Monomer Having an Ionic Dissociating Group at the Side Chain

In obtaining a super-absorbent resin of the present invention by copolymerization, use of an unsaturated monomer having an ionic dissociation group in the main or side chain, particularly at the side chain may be preferably used. Among monomers having an ionic dissociation group in the side chain, composing a super-absorbent resin of the present invention, as an unsaturated monomer having an acid group and/or salt thereof in the side chain (hereinafter abbreviated simply as a monomer), (meth)acrylic acid and/or salt thereof, as a main component may be preferably as a main component. In this case, another monomer may be used in combination, and a super-absorbent resin may be yielded only from such other monomers. Furthermore, as a monomer to be used, maleic acid (anhydride), fumaric acid, crotonic acid, itaconic acid, vinyl sulfonic acid, 2-(meth)acrylamide-2-methylpropane sulfonic acid, (meth)acryloxyalkane sulfonic acid, styrene sulfonic acid and alkali metal salt thereof, and the like can suitably be used.

Among monomers having an ionic dissociation group in the side chain, as an unsaturated monomer having a basic group and/or salt thereof in the side chain, dialkylaminoalkyl (meth)acrylate, dialkylaminoalkyl (meth)acrylamide, allylamine, diallylamine, and the like may be included.

(4) Other Monomers

In addition, a monomer other than a monomer having an ionic dissociation group in the side chain, and a monomer having a hydrocarbon group with carbon atoms of not lower than 4 in the side chain may be used as a copolymerizable component. As an example of such a monomer, (meth)acrylamide, N-vinyl-2-pyrrolidone, N-vinyl acetamide, N-vinyl foramide, N-isopropyl (meth)acrylamide, N,N-dimethyl (meth)acrylamide, 2-hydroxyethyl (meth)acrylate, methoxy-polyethylene glycol (meth)acrylate, polyethylene glycol (meth)acrylate, isobutylene, methyl (meth)acrylate, ethyl (meth)acrylate, and the like can be included as a copolymerizable component, although being not limited thereto. Ratio of the "other monomer" described herein to attain the present invention preferably is 0 to 30% by mole, more preferably is 0 to 20% by mole, particularly preferably is 0 to 10% by mole and most preferably is 0 to 5% by mole, based on total monomer amount. In addition, the ratio based on total monomer amount preferably is 0 to 30% by weight, more preferably is 0 to 20% by weight, particularly preferably is 0 to 10% by weight and most preferably is 0 to 5% by weight. Accordingly, the ratio of total amount of a monomer having an ionic dissociation group in the side chain and a monomer having a hydrocarbon group with carbon atoms of not lower than 4 in the side chain, occupying in total monomer amount, is preferably 70 to 100% by mole, more preferably is 80 to 100% by mole, particularly preferably is 90 to 100% by mole and most preferably is 95 to 100% by mole, based on total monomer amount. In addition, the ratio preferably is 70 to 100% by weight, more preferably is 80 to 100% by weight, particularly preferably is 90 to 100% by weight and most preferably is 95 to 100% by weight, based on total monomer amount.

(5) Unsaturated Monomer Having a Hydrocarbon Group with Carbon Atoms of not Lower than 4 in the Side Chain Although an unsaturated monomer having a hydrocarbon group with carbon atoms of not lower than 4 in the side chain is not particularly limited, an ethylenically unsaturated monomer having a carboxyl group having a hydrocarbon group with carbon atoms of not lower than 4 in the side chain can be preferably included, and an ester or an amide monomer obtained from an alcohol or an amine having a linear or branched or cyclic hydrocarbon group with carbon atoms of not lower than 4, and an ethylenically unsaturated monomer having a carboxyl group can be more preferably included. As a typical example of such a monomer, (meth)acrylic esters or alkyl-substituted (meth)acylamides such as butyl (meth)acrylate, cyclohexyl (meth)acrylate, benzyl (meth)acrylate, 2-ethyl-hexyl (meth)acrylate, lauryl (meth)acrylate, stearyl (meth)acrylate, isostearyl (meth)acrylate, palmityl (meth)acrylate, myristyl (meth)acrylate, capryl (meth)acrylate, cetyl (meth)acrylate, isobornyl (meth)acrylate, undecylenyl (meth)acrylate, oleyl (meth)acrylate, 2-ethyl-hexyl (meth)acrylamide, lauryl (meth)acrylamnide, stearyl (meth)acrylamide, isostearyl (meth)acrylamide, palmityl (meth)acrylamide, myristyl (meth)acrylamide, capryl (meth)acrylamide, cetyl (meth)acrylamide, isobornyl (meth)acrylamide, undecylenyl (meth)acrylamide, and oleyl (meth)acrylamide can be included. Furthermore, the ester and the amide of a similar monomer such as maleic acid, fumaric acid, and itaconic acid are also included.

Furthermore, an ester monomer may be also used, that is obtained from a carboxylic acid having a linear or branched or cyclic hydrocarbon group with carbon atoms of not lower than 4, and an ethylenically unsaturated monomer having a hydroxyl group. As typical examples of such a monomer, vinyl esters such as vinyl valerate, vinyl heptanoate, vinyl caprylate, vinyl caprate, vinyl laurate, vinyl myristate, vinyl palmitate, vinyl stearate, vinyl isostearate, vinyl undecylenate, vinyl behenate, vinyl naphthenate, vinyl linoleate, and vinyl linolenate can be included. Furthermore, the ester of a similar monomer such as hydroxyalkyl (meth)acrylate, polyethylene glycol (meth)acrylate, and allyl alcohol can be also included. In particular, a compound having an unsaturated hydrocarbon group moiety as a hydrocarbon group with carbon atoms of not lower than 4 is expected to exhibit antibacterial performance. As such an example, undecylenoxy polyethylene glycol (meth)acrylate and the like can be included, which particularly is suitably used because of further furnishing antibacterial activity.

Furthermore, an amide monomer may be also used, that is obtained from a carboxylic acid having a linear or branched or cyclic hydrocarbon group with carbon atoms of not lower than 4, and an ethylenically unsaturated monomer having an amino group. As typical examples of such a monomer, vinylamides such as caprylic acid N-vinylamide, capric acid N-vinylamide, lauric acid N-vinylamide, myristic acid N-vinylamide, palmitic acid N-vinylamide, stearic acid N-vinylamide, isostearic acid N-vinylamide, palmitic acid N-vinylamide, undecylenic acid N-vinylamide, behenic acid N-vinylamide, naphthenic acid N-vinylamide, linoleic acid N-vinylamide, and linolenic acid N-vinylamide can be included. Further, a similar monomer derived from allylamine can be also included.

A quaternary salt monomer may also be used, that is obtained from a halide having a linear or branched or cyclic hydrocarbon group with carbon atoms of not lower than 4, and an ethylenically unsaturated monomer having an amino group. As typical examples of such a monomer, quaternary salts of dialkylaminoalkyl (meth)acrylate, dialkylaminoalkyl (meth)acrylamide, vinyl amine, and allylamine, having such as heptyl group, octyl group, 2-ethylhexyl group, nonyl group, lauryl group, palmityl group, stearyl group, isostearyl group, undecylenyl group, behenyl group, naphthyl group, oleyl group, cetyl group and isobornyl group can be included.

Furthermore, an ester monomer may be also used, that is obtained from an alcohol having a linear or branched or cyclic hydrocarbon group with carbon atoms of not lower than 4, and an ethylenically unsaturated monomer having sulfonic acid group or phosphoric acid group. Heptyl ester, octyl ester, 2-ethylhexyl ester, nonyl ester, lauryl ester, palmityl ester, stearyl ester, isostearyl ester, undecylenyl ester, behenyl ester, naphthylester, oleylester, isobornylester, andcetyl ester and the like of vinyl sulfonic acid, styrene sulfonic acid, 2-(meth) acrylamide-2-methylpropane sulfonic acid, and (meth)acryloxyalkane sulfonic acid and the like can be included.

In addition, α-olefin having a linear or branched or cyclic hydrocarbon group with carbon atoms of not lower than 4 may at the side chain may also be used, and 1-nonene, 1-decene, 1-octadecene and the like can be included.

Among these monomers, esters to be obtained from an alcohol having a linear or branched or cyclic hydrocarbon group with carbon atoms of not lower than 4, and an ethylenically unsaturated monomer having a carboxyl group like (meth)acrylic acid are preferably used as the unsaturated monomer having a hydrocarbon group with carbon atoms of not lower than 4 in the side chain, and esters to be obtained from an alcohol having a linear or branched or cyclic hydrocarbon group with carbon atoms of not lower than 4, and (meth)acrylic acid are more preferable. As preferable examples thereof, lauryl (meth)acrylate, stearyl (meth)acrylate, myristyl (meth)acrylate, palmityl (meth)acrylate may be preferable.

These monomers may be used alone or as in a mixed form of two or more kinds, as appropriate.

When a copolymerization method is adopted to obtain a super-absorbent resin of the present invention, although a relative weight ratio of an unsaturated monomer (A) having an ionic dissociation group in the side chain, and an unsaturated monomer (B) having a hydrocarbon group in the side chain may be (A):(B)=100:0 (composed of only (A)), it is preferably is in a range of (A):(B)=50:50 to 99:1, more preferably is in a range of (A):(B)=60:40 to 98:2, further preferably is in a range of (A):(B)=65:35 to 97:3, and particularly preferably is in a range of (A):(B)=70:30 to 96:4, and most preferably is in a range of (A):(B)=80:20 to 95:5. Within such a relative weight ratio, the resultant super-absorbent resin can keep a good balance between osmotic pressure derived from the ionic dissociation group, and aggregation derived from the hydrocarbon group and chemical cross-linking at vicinity of the surface thereof.

As for molar ratio, although the super-absorbent resin may be composed of only (A) (100% by mol), it is preferably is in a range of (A):(B)=70:30 to 99.7:0.3, more preferably is in a range of (A):(B)=80:20 to 99.5:0.5, and most preferably is (A):(B)=90:10 to 99:1. Within such a molar ratio, the resultant super-absorbent resin can keep a good balance between osmotic pressure derived from the ionic dissociation group, and aggregation derived from the hydrocarbon group and chemical cross-linking at vicinity of the surface thereof.

As for a polymer having a hydrocarbon group with carbon atoms of not lower than 4, obtained by reacting a hydrocarbon group with carbon atoms of not lower than 4 to a reactive group such as carboxyl group, sulfonic acid group, phosphoric acid group, and amino group of a polymer, the preferable range is defined by molar ratio of the repeating unit.

A polymer in this case is not especially limited, as long as it has a repeating unit of an ionic dissociation group in the main or side chain, as a main component and Poly (meth) acrylic acid, polystyrene sulfonic acid, poly-2-acrylamide-2-methylpropane sulfonic acid, polymaleic acid, carboxymethyl cellulose, carrageenan, gellan gum, xanthan gum, polyethylenimine, polyallylamine, polydiallylamine, polydialkylaminoalkyl acrylate, polydialkylaminoalkyl acrylamide, and a (partially) neutralized compound thereof can be included, for example. Polyethyleneimine is a typical example of one having a repeating unit of an ionic dissociation group in the main chain. As a compound to introduce a hydrocarbon group with carbon atoms of not lower than 4, a compound having aldehyde group, epoxy group, amino group, and hydroxyl group, as well as a hydrocarbon group with carbon atoms of not lower than 4 may be used.

(6) Method for Polymerization and Polymerization Solution

In the present invention, bulk polymerization, precipitation polymerization or solution polymerization can be carried out, however, in view of operational safety, precipitation polymerization or solution polymerization is preferably carried out. A monomer concentration in the solution polymerization can be determined depending on temperature of the solution or kind of the monomer, and should not be especially limited. Preferably, it is 10 to 70% by weight and more preferably is 20 to 60% by weight. As a solvent used in the solution polymerization, water; a lower alcohol such as methanol, ethanol and 2-propanol or a mixed solution of these lower alcohols with water; and a lower ketone such as acetone and methyl ethyl ketone or a mixed solution of these lower ketones with water can be used, however, not limited thereto.

Precipitation polymerization is a polymerization method as described in JP-A-60-71623, or in Radical Polymerization Handbook, p. 264 (published from N. T. S. Co., Ltd. in 1999), wherein a monomer can be soluble in a solvent but a polymer obtained by polymerization thereof becomes insoluble in a solvent to be precipitated as fine particles, which easily yields a polymer only by removal of a solvent. A monomer concentration in the precipitation polymerization is preferably in a range of 1 to 50% by weight, further preferably is 5 to 30% by weight, and most preferably is 10 to 25% by weight. In the case of carrying out precipitation polymerization in a particularly high concentration, the polymerization preferably is carried out in the coexistence of polyoxyethylene having a molecular weight of 2,000 to 20,000, specifically in the coexistence of such as a copolymer of ethylene oxide and propylene oxide, in an amount of 0.5 to 10% by weight, based on the monomer. A solvent used in the precipitation polymerization is difficult to be specified because of dependency on kind of a monomer used. Such a solvent should be selected that dissolves a monomer and does not dissolve a polymer generated by polymerization. As typical examples of the solvent for precipitation polymerization, alkanes with carbon atoms of 5 to 10, for example, hexane and pentane; cycloalkanes with carbon atoms of 5 to 10, for example, cyclohexane; benzene or alkyl-substituted benzene, toluene and xylene; alkkylcarboxylates with carbon atoms of 1 to 6 in the alkyl group, and with carbon atoms of 1 to 6, preferably 2 to 6 in the carboxylate moiety, for example, ethyl acetate and methyl acetate, and haloalkanes with carbon atoms of 1 to 2 and at least 2 or more halogen groups, for example, dichloroethane and the like may be cited.

In initiating the polymerization, the polymerization initiator described below may be used for initiation. As well as the polymerization initiator, activated energy ray such as ultraviolet ray, electron beams or γ-ray may be used alone or in combination with the polymerization initiator. A temperature at polymerization initiation depends on kind of the polymerization initiator used. It is preferably in the range of 15 to 130° C., and more preferably in the range of 20 to 120° C.

The polymerization conditions according to the present invention are not especially limited so long as a desired super-absorbent resin can be obtained from the monomers as described above. Generally, it is in the range of 0 to 150° C., more preferably 20 to 100° C., for one minute to 10 hours, more preferably 1 to 3 hours, optionally in the presence of a chain transfer agent and/or a surfactant.

(7) Polymerization Initiator

As a polymerization initiator used in initiating polymerization of the monomer to obtain a super-absorbent resin used in the present invention, any compound having radical generation performance such as an azo compound and a peroxide may be adopted, for example. Typically, radical polymerization initiators such as potassium persulfate, ammoniumpersulfate, sodiumpersulfate, potassiumperacetate, sodium peracetate, potassium percarbonate, sodium percarbonate, benzoyl peroxide, capryl peroxide, t-butyl hydroperoxide, hydrogen peroxide, 2,2'-azobis(2-amidinopropane)dihydrochloride, 2,2'-azobisisobutyronitrile, 2,2'-azobis(2-methylbutyronitrile), and 2,2'-azobis(2,4-dimethylvaleronitrile); and photo-polymerization initiators such as 2-hydroxy-2-methyl-1-phenyl-propane-1-one can be used. These polymerization initiators can be used singly or in a mixed form of two or more members. An amount of the polymerization initiator used is, in view of absorption properties, 0.001 to 2% by mole, preferably is 0.01 to 0.2% by mole, based on total monomer.

The polymerization initiator in an amount of less than 0.001% by mole would increases residual unreacted monomers, while the polymerization initiator in an amount exceeding 2% by mole would make control of polymerization difficult, which would not be preferable.

(8) Chain Transfer Agent

In the present invention, a chain transfer agent may be optionally used in the polymerization. By polymerization in the presence of a chain transfer agent, in addition to the unsaturated monomer and the polymerization initiator, a molecular weight of the resultant resin can be controlled so as not to become too high. As a result, not only absorption capacity of the resultant super-absorbent resin to saline solution can be adjusted but also it leads to be adjusted so that fast solubility in water can be attained. In particular, when a solvent used in polymerization is water or ketone, a chain transfer agent can be suitably used.

A chain transfer agent used in polymerization according to the present invention is not especially limited as long as it dissolves in a solvent or an ethylenically unsaturated monomer. Typically, thiols, thiolates, alcohols, amines, hypophosphites, and the like can be included. Specifically, mercaptoethanol, mercaptopropanol, dodecylmercaptan, thioglycols, thiomalic acid, 3-mercaptopropionic acid, methanol, ethanol, isopropanol, sodiumhypophosphite, formic acid, and salts thereof can be used. These chain transfer agents may be used alone or in a mixed form of 2 or more members selected from the group. In view of effects thereof, a hypophosphite salt such as sodium hypophosphite preferably may be used.

An amount of a chain transfer agent used may depend on kind of the chain transfer agent and concentration of a monomer solution. It is generally 0 to 1% by mole, and preferably is 0 to 0.3% by mole, based on total monomer. The use amount exceeding 1% by mole would increase an amount of components dissolved in saline solution, which lowers absorption capacity to saline solution, which would not be preferable.

A weight average molecular weight required to a super-absorbent resin of the present invention may depend on property of an ionic dissociation group, property of a hydrocarbon group and ratio of these groups and neutralization ratio, and the like. It is preferably in a range of 10,000 to 2,000,000, more preferably is in a range of 20,000 to 1,000,000, and most preferably is in a range of 30,000 to 800,000.

In this invention, a weight average molecular weight is determined by the following method. Specifically, the weight average molecular weight is a value which is determined by preparing an unneutralized super-absorbent resin (i.e., a super-absorbent resin having a neutralization ratio of 0%), dissolving the super-absorbent resin in a solvent such as methanol, ethanol, and the like, and subjecting the resultant solution to GPC (Gel Permeation Chromatography). In the case of a neutralized super-absorbent resin, a super-absorbent resin which has been treated with an acidic substance or a basic substance so as to give a neutralization ratio of 0% is used as the unneutralized super-absorbent resin.

(9) Surfactant

Since the super-absorbent resin of the present invention has as a main component a repeating unit having an ionic dissociation group in the main or side chain, and preferably has a hydrocarbon group in the side chain, polarity of both functional groups largely differs. Therefore, depending on the kind of a solvent used in practical synthesis, a surfactant is preferably used to promote dispersion. For example, in the case of copolymerization of a monomer having an ionic dissociation group in the side chain, and a monomer having a hydrocarbon group in the side chain, in water or an organic solvent or a mixed solvent thereof, or in the case of introducing a hydrocarbon group into a polymer having as a main component a repeating unit having an ionic dissociation group in the main or side chain, the polymerization or reaction preferably is carried out particularly in the coexistence of a surfactant.

A surfactant used in this case is not especially limited and for example, the following ones may be included.

Salts of alkyl sulfate, fatty acid salts: for example, sodium stearate, sodium laurate, sodium dodecyl sulfate; alkylbenzene sulfonic acid salts, alkylnaphthalene sulfonic acid salts, alkylsulfosuccinic acid salts: for example, sodium dodecylbenzenesulfonate, sodium dialkyl sulfosuccinate; polyoxyethylene alkylether sulfuric acid ester salts: for example, polyoxyehylene lauryl ether sodium sulfate; alkaline phosphoric acid esters: for example, dodecyl hydrogen phosphate, polyoxyethylene alkyl ether potassium phosphate; fluoro emulsifiers: for example, perfluoroalkyl sulfate, etc.; alkylamine hydrochloride: for example, dodecylamine hydrochloride, tridecylamrine hydrochloride; polyoxyethylene alkyl ethers, sorbitan fatty acid esters, polyoxyalkylene alkyl ethers, polyoxyethylene sorbitan fatty acid esters, polyoxyethylene sorbitol fatty acid esters, glycerin fatty acid esters, polyoxyethylene fatty acid esters, polyoxyethylene alkylamines, and the like can be included.

As an amount of the surfactant used, it is enough by amount such as being capable of dispersing (micelle formation) a monomer or a compound. The used amount preferably is 0 to 50% by weight, more preferably is 0 to 30% by weight, particularly preferably is 0 to 20% by weight, particularly preferably is 0 to 10% by weight, and most preferably is 0 to 5% by weight, based on the total amount of a polymer or monomer.

(10) Neutralization Ratio and Neutralization Method

An ionic dissociation group (an acid group or a basic group) preferably is neutralized in view of property and pH, to obtain a super-absorbent resin of the present invention, although it may depend on property of the ionic dissociation group to be used. The neutralization ratio thereof is usually 30 to 100% by mole, more preferably is 40 to 90% by mole, and most preferably is 50 to 90% by mole, based on the total ionic dissociation groups. Neutralization of the acid group or basic group may be carried out in a monomer state, a polymer state or in combined state thereof. Further, neutralization of the acid group or basic group may be carried out at any stage as of before polymerization, during polymerization or after polymerization.

By neutralizing the acid group or basic group, osmotic pressure by ion dissociation increases, and absorption capacity to saline solution and solubility in water can be expected-tobe promoted. In particular, when a carboxyl group is used as acid group or amino group is used as basic group, the tendency is significantly observed. In addition, when a sulfonic acid group is used as acid group, non-neutralization incurs too low pH of a polymer, causing skin roughness in use as a diaper, which is not preferable. In the present invention, pH range of a polymer preferably is controlled within a range of 4.0 to 8.0, and more preferably within a range of 5.0 to 7.0.

In this connection, when a salt form is taken by neutralization of the acid group, alkali metal salt, alkali earth metal salt, ammonium salt are included. In view of performance, industrially easy availability, safety of the resultant super-absorbent resin, and the like, sodium salt, potassium salt, lithium salt, and ammonium salt are preferably formed.

In addition, as an alkali metal compound used for neutralizing the acid group to partially or wholly form the alkali metal salt, alkali metal hydroxide (sodium hydroxide, potassium hydroxide, lithium hydroxide, and the like), alkali metal carbonate (sodium carbonate, sodium bicarbonate, and the like), and the like are included.

When a salt form is taken by neutralization of the basic group, hydrochloride salt, sulfate salt, phosphate salt, and carboxylate salt are included. As typical examples of the carboxylate salt, acetate, propionate, lactate, and the like are included, however, not limited thereto.

In addition, although an acid used for neutralizing the basic group to partially or wholly form the salt can be suitably selected depending on the desired salt form, hydrochloric acid, sulfuric acid, phosphoricacid, acetic acid, propionic acid, lactic acid, and the like are included.

As a neutralization method of a polymer, a method is preferably used, which comprises the compound forming a salt to a polymer which is present as gel-like state, a viscous solution or a dried solid, and then kneading the resultant mixture sufficiently as in a kneader or a meat chopper. In addition, when a particulate super-absorbent resin (water-absorbent) is to be obtained in the present invention, neutralization temperature is preferably 10 to 100° C., and more preferably 20 to 90° C. Further, uniformity preferably is shown by a first neutralization coefficient (specified by neutralization ratio of 200 particles) as described in claim 1 of U.S. Pat. No. 6,187,872, of not higher than 10. Further, when a fibrous super-absorbent resin (water-absorbent) is to be obtained in the present invention, it is preferably to add the compound forming a salt in an aqueous solution state to the super-absorbent resin, and left standing to carry out neutralization thereof.

(11) Drying

When the polymer expresses a viscous solution or a gel-like substance, it may be subsequently subjected to drying. Drying is usually carried out at a temperature in the range of 20° C. to 250° C., preferably at 40° C. to 220° C. and more preferably at 50° C. to 200° C. Drying time may depend on surface area and amount of volatile component of a polymer, and kind of a dryer, and may be selected so that desired amount of volatile component can be obtained.

A amount of volatile component (specified by content of volatile portions such as water contained in a super-absorbent resin, and measured as reduced amount by drying at 180° C. for 3 hours) of a super-absorbent resin of the present invention is not especially limited. It preferably is such level as provides particles (powder) or fiber showing fluidity even at room temperature, more preferably provides a particle or fibrous state having a amount of volatile component in a range of 0 to 40% by weight, more preferably 0 to 30% by weight, further preferably 0 to 20% by weight, and most preferably is 0 to 10% by weight. Higher amount of volatile component would not only incur trouble in production due to poor fluidity, but also would inhibit crushing of a super-absorbent resin or would be out of control within specified particle size distribution. In addition, in such a case, absorption capacity without load to saline solution would be unduly lowered and features by the present invention would not be satisfied.

As a method for drying to be used, various methods can be adopted so that desired amount of volatile component is obtained, without any limitation, such as heating drying, hot air drying, reduced pressure drying, infrared-ray drying, microwave drying, dehydration by azeotropy with a hydrophobic organic solvent, and drying under high humidity using high temperature steam.

(12) Form of a Super-Absorbent Resin-Crushing, Classification and Particle Size Control Although a form of a super-absorbent resin of the present invention obtained by the above production method is not especially limited, it is preferably in a particulate or fibrous form. In this case, as long as it can be handled as a particulate or fibrous substance, any form including spherical shape, fibrous shape, bar-like shape, nearly spherical shape, flat shape, irregular shape, granulated particle shape, and particle having porous structure can be used.

When a super-absorbent resin of the present invention is made into particulate shape, adjustment to specified particle size is preferable.

When a super-absorbent resin of the present invention takes a particulate shape, a particle diameter thereof is controlled, as mass average particle diameter, usually in the range of 150 to 3,000 μm, preferably 150 to 1,000 μm, more preferably 200 to 600 μm, and particularly preferably 200 to 500 μm. It may be also preferably controlled so as that the super-absorbent resin contains particles having a particle diameter less than 150 μm in an amount as small as possible. Typically, the ratio of particles having a particle diameter less than 150 μm contained in the super-absorbent resin is 0 to 30% by weight, preferably 0 to 15% by weight, more preferably 0 to 10% by weight, and most preferably 0 to 5% by weight, based on the total weight of the super-absorbent resin.

The particle diameter over the above range would require excess time till being dissolved into water, which could induce clogging of a drainage pipe when flushed down a toilet basin, and the like. In addition, the particle diameter below the range may deteriorate water absorption performance or cause drop of a super-absorbent resin when an absorbing core is produced, which would not be preferable.

Logarithmic standard deviation ($\sigma \zeta$) of the particle size distribution preferably is set to be 0.20 to 0.60, more preferably 0.20 to 0.50, and particularly preferably 0.20 to 0.40.

Logarithmic standard deviation over the range may provide variation in time till dissolving each particle in water, which could generate partially undissolved portions, and thus not preferable. In addition, logarithmic standard deviation below the range would make production of super-absorbent resin difficult, resulting in high cost.

Particle size adjustment may be performed so that desired particle size can be obtained by crushing and classification after solution polymerization, after neutralization step and after drying.

When a super-absorbent resin of the present invention is fabricated in a fiber form, a spinning method as described in WO 93/24684, WO 94/04724 and JP-B-2-2969 can be adopted. According to this method, an aqueous solution of a polymer of the present invention may be extruded from a nozzle for spinning, and quickly thereafter, subjected to drying at a temperature of 150° C. to 250° C. and forming in fiber shape. In this case, drying time may be varied with surface area and amount of volatile component of a polymer, and kind of a dryer, ad may be selected so that desired amount of volatile component can be attained. An average fiber diameter of fiber in this case is in a range of 10 μm to 1,000 μm, 10 μm to 800 μm, 10 μm to 500 μm, 10 μm to 300 μm, and 10 μm to 150 μm, preferably in this order. Because fiber is long, it has merit that drop from an absorbing core is fewer than the case of a particulate form, even when average fiber diameter is small. In this connection, average fiber diameter is determined as average of diameter of 100 fibers measured under a microscope. When a super-absorbent resin of the present invention takes a fiber form, length of fiber is not especially limited and varied with applications and average diameter of fiber. It is preferably in the range of 100 to 1,000,000 μm, more preferably 100 to 100,000 μm, particularly preferably 100 to 10,000 μm.

In the use of a conventionally known ion-sensitive binder, such a method has been carried out, wherein a polymer solution is sprayed as a binder on an absorbing core web formed, and dried to produce an absorbing core with high strength. It, however, has had problems that when a large quantity of the polymers was introduced in the absorbing core, the absorbing core became hard, and acquisition rate of the solution into the absorbing core was lowered, as well as introduction of a large quantity of the polymers was not practical due to increasing load at the subsequent drying step. On the contrary, according to the present invention, by fabricating a super-absorbent resin into a particulate or fibrous form, hydrophilic fiber and a super-absorbent resin composing an absorbing core can be mixed in dry state or humidified state, which in turn is capable of introducing a super-absorbent resin efficiently and in large quantity into the absorbing core. In particular, particulate or fibrous shape of a super-absorbent resin can secure space among particles or fibers of a super-absorbent resin, which can provide effects of excellent fluid-acquisition speed into the absorbing core.

(13) Surface Cross-Linking Treatment

In the present invention, so-called surface cross-linking treatment may be carried out for further introducing cross-linking at the vicinity of the surface of the resultant super-absorbent resin. By the surface cross-linking treatment, diffusion or dry feeling when a super-absorbent resin absorbs fluid, and absorption under pressure can be improved. Although in some cases, cross-linking introduced by the surface cross-linking treatment is based on chemical bond, because the cross-linking is just only at the vicinity of the particle surface, the characteristics can be improved without impairing features of the present invention. In addition, degree of surface cross-linking may be adjusted, as appropriate, depending on kind or amount of a cross-linking agent, reaction temperature or time, and the like.

A surface cross-linking agent which can be used in the present invention is not especially limited, and for example, those exemplified in U.S. Pat. No. 6,228,930, U.S. Pat. No. 6,071,976, U.S. Pat. No. 6,254,990, and the like can be used. More specifically, polyvalent alcohol compounds such as mono-, di-, tri-, tetra- or polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butane-diol, 1,3-butandiol, 1,5-pentanediol, 1,6-hexanediol, and 1,2-cyclohexanedimethanol; epoxy compounds such as ethylene glycol diglycidyl ether, or glycidol; polyvalent amine compounds such as ethylene diamine, diethylene triamine, triethylene tetramine, tetraethylene pentamine, pentaethylene hexamine, polyethylene imine, and polyamide polyamine; haloepoxy compounds such as epichlorohydrin, epibromohydrin, and α-methylepichlorohydrin; condensates of the polyvalent amine compounds and the haloepoxy compounds; oxazolidinone compounds such as 2-oxazolidinone; alkylene carbonate compounds such as ethylene carbonate, and the like are included. These cross-linking agents may be used alone or in a mixed form of 2 or more members. For the effect of the present invention to sufficiently be fulfilled, polyvalent alcohols may be preferably used as an essential component among these surface cross-linking agents. As polyvalent alcohols, one having carbon atoms of 2 to 10 is preferable, and one having carbon atoms of 3 to 8 is more preferable.

Although an amount of the surface cross-linking agent used depends on a compound to be used or a combination thereof, and the like, it preferably is in the range of 0.001 to 10% by weight, and more preferably 0.01 to 5% by weight, based on a super-absorbent resin.

When surface cross-linking is carried out in the present invention, water is preferably used. In this case, although an amount of water used depends on amount of volatile component of a super-absorbent resin to be used, it preferably is in the range of 0.5 to 20% by weight, and more preferably 0.5 to 10% by weight, based on a super-absorbent resin. In addition, a hydrophilic organic solvent may be used as well as water. As typical example of the hydrophilic organic solvent, alcohols such as methyl alcohol, ethyl alcohol, propyl alcohol, isopropyl alcohol, butyl alcohol, isobutyl alcohol, t-butyl alcohol; ketones such as acetone, methyl ethyl ketone; ethers such as dioxane, alkoxy(poly)ethylene glycol, tetrahydrofuran; amides such as ε-caprolactam, N,N-dimethylformamide; sulfoxides such as dimethyl sulfoxide; polyvalent alcohols such as ethylene glycol, diethylene glycol, propylene glycol, triethylene glycol, tetraethylene glycol, 1,3-propanediol, dipropylene glycol, 2,2,4-trimethyl-1,3-pentanediol, glycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, pentaerythritol, solbitol, and the like may be cited. These hydrophilic organic solvents can be used singly or in a mixed form off two or more members. In the case of using a hydrophilic organic solvent, an amount of the hydrophilic organic solvent used preferably is in the range of 0 to 10% by weight, more preferably 0 to 5% by weight, and further more preferably 0 to 3% by weight, based on a super-absorbent resin.

When surface cross-linking is carried out in the present invention, such a method preferably is adopted, which comprises mixing water and/or a hydrophilic organic solvent with a surface cross-linking agent in advance, and then spraying or mixing by dropping the aqueous solution onto a super-absorbent resin In this case, the spraying method is more preferable. Size of the droplet to be sprayed preferably is, as average particle diameter, in the range of 0.1 to 300 μm, and more preferably 0.1 to 200 μm.

As mixing equipment used in mixing a super-absorbent resin and a surface cross-linking agent, water or a hydrophilic organic solvent, one having large mixing force is preferably used to ensure uniform mixing thereof. As the mixing equipment, for example, a cylinder-type mixer, a double wall cone mixer, a high speed stirring type mixer, a V-shaped mixer, a ribbon-type mixer, a screw-type mixer, a double arm-type kneader, a crushing-type kneader, a rotation-type mixer, an air flow type mixer, a turbulizer, a batch type Rhedige mixer, a continuous type Rhedige mixer, and the like can be suitably used.

A super-absorbent resin after mixed with the surface cross-linking agent preferably is subjected to heat-treatment. Heating temperature (heat medium temperature or material temperature) preferably is in the range of 50 to 250° C. and more preferably is in a range of 100 to 250° C., and heating time preferably is in a range of 1 minute to 2 hours. Suitable examples of combinations of heating temperature and heating time are at 180° C. for 0.1 to 1.5 hours, or at 200° C. for 0.1 to 1 hour.

(14) Other Additives

In the present invention, components exemplified in the following (A) to (F) may be added as trace components to furnish various functions to a super-absorbent resin of the present invention. In this case, the components exemplified in the following (A) to (F) may be used singly or in a mixed form of 2 or more members or at least one component (A) to (F) may be used in combination.

(A) Plant Extracts

A super-absorbent resin relevant to the present invention may be formulated with a plant extract in the following amount to fulfill deodorant property. The plant extract which can be used in the present invention preferably is at least one member selected among polyphenol, flavone and their derivatives, caffeine, tannin, tannicacid, galla, gallnut and gallic acid.

As a plant containing such a plant extract which can be used in the present invention, for example, Theaceous plant such as camellia, HIKASAKI and Mokkoku; Gramineous plant such as rice plant, Sasa-bamboo, bamboo, corn and wheat; Rubiaceous plant such as coffee; and the like may be included.

As a form of the plant extract which can be used in the present invention, extracts (essential oil) extracted from plants, plant itself (plant powder), plant residue and extract residue by-produced in the production step in plant fabrication industry or food processing industry, and the like are included, however, not limited thereto.

(B) Polyvalent Metal Salts

A super-absorbent resin relevant to the present invention may be formulated with a polyvalent metal salt, in particular, a polyvalent metal salt of organic acid in the following amount to improve powder fluidity and to prevent blocking under humid conditions. The polyvalent metal salt of organic acid to be used and a mixing method thereof are exemplified, for example, in WO 2004/069936, and the polyvalent metal salt of organic acid having carbon atoms of not less than 7 in its molecule, which can be used in the present invention, includes metal salts other than alkali metal salts of fatty acids, petroleum acids, polymer-based acids, and the like.

As an organic acid composing the polyvalent metal salt of organic acid, long chain or branched chain fatty acids such as caproic acid, octylic acid, octynic acid, decanoic acid, lauric acid, myristic acid, palmitic acid, oleic acid, stearic acid, beef tallow acid and fatty acid of hydrogenated castor oil; petroleumacids such as benzoic acid, myristicinic acid, naphthenic acid, naphthoic acid, and naphthoxyacetic acid; polymer-based acids such as poly(meth)aclylic acid, and polysulfonic acid can be exemplified. Preferably, an organic acid having a carboxyl group in its molecule may be used, and fatty acids such as caproic acid, octylic acid, octynic acid, decanoic acid, lauric acid, myristic acid, palmitic acid, oleic acid, stearic acid, beef tallow acid or fatty acid of hydrogenated castoroil may be more preferably used. Further more preferably, fatty acids having no unsaturated bonds in its molecule, for example, caproic acid, octylic acid, decanoic acid, lauric acid, myristic acid, palmitic acid, oleic acid, stearic acid may be used. Most preferably, long chain fatty acids having carbon atoms of not less than 12, and no unsaturated bonds in its molecule, for example, lauric acid, myristic acid, palmitic acid, oleic acid, and stearic acid may be used.

(C) Inorganic Fine Particles

A super-absorbent resin relevant to the present invention may be formulated with inorganic fine particles, in particular, water-insoluble inorganic fine particles to prevent blocking under humid conditions. As inorganic fine particles which can be used in the present invention, specifically for example, metal oxides such as silicon dioxide, and titanium oxide; silicic acid (silicates) such as natural zeolite, and synthetic zeolite; kaolin, talc, clay, bentonite; and the like may be included. Among these, silicon dioxide and silicic acid (silicates) is morepreferable, and silicondioxide and silicic acid (silicates) having an average particle diameter as measured by a Coulter counter method of 0.001 to 200 μm are further preferable.

(D) Composite Hydrated Oxides

A super-absorbent resin relevant to the present invention may be formulated with a composite hydrated oxide containing zinc and silicon, or zinc and aluminum (for example, one exemplified in WO 2005/010102) to provide excellent fluidity under humid conditions (powder fluidity after a super-absorbent resin absorbed moisture) and furthermore to fulfill excellent deodorant performance.

(E) Addition of a Chelating Agent

A super-absorbent resin of the present invention may be formulated with a chelating agent, in particular, a polyvalent carboxylic acid and salt thereof. By this formulation, decomposition of a super-absorbent resin caused by components contained in urine or blood can be suppressed.

A chelating agent which can be used in a particulate water-absorbing agent of the present invention preferably include a chelating agent having high ion sequestering ability or chelating ability to Fe or Cu, specifically, having a stability constant of not smaller than 10, preferably not smaller than 20 to an Fe ion, and further preferably a polyvalent aminocarboxylic acid and salt thereof, and particularly preferably, an aminocarboxylic acid having not less than 3 carboxyl groups and salt thereof.

Specifically, these polyvalent aminocarboxylic acids include diethylenetriamine pentaacetic acid, triethylenetetraamine hexaacetic acid, cyclohexane-1,2-diamine tetraacetic acid, N-hydroxyethylethylenediamine triacetic acid, ethylene glycol diethyl ether diamine tetraacetic acid, ethylene diamine tetrapropionic acetic acid, N-alkyl-N'-carboxymethyl asparatic acid, N-alkenyl-N'-carboxymethyl asparatic acid, and alkaline metal salts, alkaline earth metal salts, ammonium salts or amine salts thereof. Among them, diethylenetriamine pentaacetic acid, triethylenetetraamine hexaacetic acid, N-hydroxyethylethylenediamine triacetic acid and salt thereof may be most preferable.

In the present invention, an amount of the chelating agent, in particular, the polyvalent aminocarboxylic acid, to be used is, as a trace component, usually in the range of 0.00001 to 10 parts by weight, and preferably 0.0001 to 1 part by weight, based on 100 parts by weight of a super-absorbent resin as a main component. The used amount over 10 parts by weight would not provide effects comparable to its amount and thus not only uneconomical but also generates a problem of reduced absorption amount. On the other hand, the amount less than 0.00001 parts by weight would not provide sufficient addition effects.

(F) Others

The addition of other additives such as an antibacterial agent, a water-soluble polymer, a water-insoluble polymer, water, organic fine particles, and the like is arbitrary, as long as a super-absorbent resin of the present invention can be obtained.

In particular, by the addition and mixing of water or a water-soluble polymer into a super-absorbent resin of the present invention, so-called granulated particles can be formed, wherein a plurality of particles aggregate to form one particle.

An amount of these (A) to (F) additives used is, as the addition amount of one kind thereof, usually in the range of 0 to 10 parts by weight, preferably 0.001 to 5 parts by weight, and further preferably 0.002 to 3 parts by weight, based on 100 parts by mass of a super-absorbent resin. Usually, the amount less than 0.001 parts by weight would not provide sufficient effects or additional function, while the amount over 10 parts by weight would not provide effects comparable to the addition amount or may incur lowering of absorption performance.

(15) Super-Absorbent Resin of the Present Invention

An ion-sensitive super-absorbent resin of the present invention produced by the production methods 1 to 4, and the like, as one of the production method, is a novel super-absorbent resin showing novel performance which has not been shown conventionally.

Specifically, a super-absorbent resin of the present invention is an ion-sensitive super-absorbent resin, preferably a particulate or fibrous ion-sensitive super-absorbent resin, having as a main component a repeating unit having an ionic dissociation group in its main or side chain, wherein a) the absorption capacity without load to saline solution (CRCs) for 4 hours thereof is not smaller than 10 g/g, and b) solubility in ion-exchanged water is not lower than 50% by weight.

A super-absorbent resin of the present invention has absorption capacity without load to saline solution for 4 hours of 10 to 100 g/g, more preferably 12 to 80 g/g, further preferably 15 to 60 g/g, further preferably 18 to 60 g/g, and most preferably 20 g/g to 60 g/g. Control of the absorption capacity may be carried out by controlling the polymerization conditions, drying conditions, surface-crosslinking treatment conditions, length or introduction ratio of a hydrocarbon group and neutralization ratio. The absorption capacity lower than 10 g/g would require more amount used in an absorbing core, which is not economical and not preferable. The "a) absorption capacity without load to saline solution (CRCs) for 4 hours" as used herein is referred to as a value which is determined in the following Examples.

"b) Solubility in ion-exchanged water", as will be described in Examples later, represents a ratio of polymer which can pass through a wire mesh within a specified period, when a super-absozbent resin is dispersed in ion-exchanged water while stirring, and after 30 minutes subjected to transfer operation on a 150 μm size wire mesh. By this value, the amount of polymer dissolved in water can be specified, and easiness of flow in a drainage pipe, and the like can be judged. A range of solubility in ion-exchanged water preferably is not lower than 50% by weight and not higher than 100% by weight, preferably not lower than 70% by weight and not higher than 100% by weight, more preferably not lower than 80% by weight and not higher than 100% by weight, particularly preferably not lower than 90% by weight and not higher than 100% by weight, and most preferably not lower than 95% by weight and not higher than 100% by weight.

The solubility in ion-exchanged water outside the range would induce swelling of a super-absorbent resin in a drainage pipe when it is flown into a flushing toilet, and the like, and could also induce clogging of the drainage pipe and thus not preferable.

In addition, the present invention has the following features:

c) Absorption Capacity without Load to Ion-Exchanged Water (CRCw) for 4 Hours

The super-absorbent resin of the present invention has absorption capacity without load to ion-exchanged water for 4 hours preferably not exceeding absorption capacity without load to saline solution for 4 hours. More preferably, the absorption capacity without load to ion-exchanged water for 4 hours is not smaller than 0 and not larger than 20 g/g, further preferably not smaller than 0 and not larger than 15 g/g, particularly preferably not smaller than 0 and not larger than 10 g/g, and most preferably not smaller than 0 and not larger than 5 g/g, while satisfying the above relationship.

When absorption capacity of a super-absorbent resin to water can be controlled within this range, there is no danger of clogging when it is flown into a flushing toilet, and the like.

d) pH

The super-absorbent resin of the present invention preferably has a specific pH (specified in 400.1-99) by EDANA (European Disposable And Nonwoven Association), in the range of 4.0 to 8.0, further preferably 4.5 to 7.5, and most preferably 5.0 to 7.0.

When pH is over this range, the super-absorbent resin would incurs skin roughness or irritation, when it is used in a disposable diaper or a sanitary napkin, and thus not preferable.

(16) Absorbing Goods/Absorbing Core

The super-absorbent resin of the present invention, in view of its unique properties, can be used as an ion-sensitive thickening agent or an ion-sensitive binder, as well as used as an ion-sensitive absorbing agent used in an absorbing goods, and the applications thereof are not especially limited. For example, the super-absorbent resin can be used in an absorbing goods which can absorb excrement, body fluid, particularly urine or blood, such as a disposable diaper and a sanitary napkin, and an absorbing core used therein.

The absorbing core of the present invention may be obtained by using the super-absorbent resin. In this connection, an absorbing core of the present invention means an absorbing material formed by a super-absorbent resin and a hydrophilic fiber as main components. A content of a super-absorbent resin (core concentration) in an absorbing core of the present invention preferably is in the range of 5 to 100% by weight, more preferably 10 to 100% by weight, particularly preferably 15 to 100% by weight, and most preferably is 20 to 100% by weight, based on total weight of the super-absorbent resin and the hydrophilic fiber.

In addition, an absorbing core of the present invention has preferably a thickness of 0.1 to 10 mm.

Further, absorbing goods of the present invention is one equipped with the absorbing core of the present invention described above, a surface sheet having fluid permeability and a back sheet having fluid non-permeability.

In a method for producing absorbing goods of the present invention, for example, absorbing goods, in particular a disposable diaper for adults or a sanitary napkin, may be prepared by blending or sandwiching a fiber substrate and a super-absorbent resin to prepare an absorbing core, and sandwiching the absorbing core between a substrate (surface sheet) having fluid permeability and a substrate (back sheet) having fluid non-permeability, and, if necessary, by furnishing elastic parts, a diffusion layer, a pressure sensitive adhesive tape, and the like. Such an absorbing core is compression molded so as to have a density of 0.06 to 0.50 g/cc and a basic weight in a range of 0.01 to 0.20 $g/cm^2$. In this connection, as the fiber substrate to be used, hydrophilic fiber, for example, crushed wood pulp and others, cotton linter or cross-linked cellulose fiber, Rayon, cotton, wool, acetate, vinylon, and the like may be exemplified. Preferably is those airlaid thereof. In particular, to utilize characteristics by the present invention, the absorbing core or absorbing goods preferably is composed of material dispersible into water.

In view of convenience, when all components of absorbing goods are dispersible into water, they can be flown directly into a toilet after use. In addition, when only an absorbing core is dispersible into water, only an absorbing core can be taken out after use to flow into a toilet, and a surface sheet or a back face sheet may be designed to be recyclable.

The super-absorbent resin of the present invention is one showing unique and novel absorption characteristics. Absorbing goods containing such a super-absorbent resin is not especially limited, and specifically includes hygienic goods such as a disposable diaper for adults, a disposable diaper for children, a sanitary napkin, so-called an incontinence pad and the like. By the effects by the super-absorbent resin of the present invention being present in absorbing goods, leakage amount from absorbing goods can be reduced, use feeling and dry feeling can be made excellent, and load of a person wearing absorbing goods and care-givers largely be reduced, along with such convenience can be furnished that absorbing goods can be flown in a toilet.

EXAMPLES

Examples and Comparative examples will be specifically explained below, however, the present invention is by no means limited to these Examples. In the following Examples, the term "part" represents "part by weight", unless otherwise specified.

In this connection, various performances of a super-absorbent resin and absorbing goods were measured by the following methods. In addition, all electric appliances used in the Examples are used under conditions of 100 V and 60 Hz. Further, a super-absorbent resin and absorbing goods were used, unless otherwise specified, under conditions at 25° C.±2° C. and a relative humidity RH of 50%. As saline solution, an aqueous solution of sodium chloride of 0.90% by weight was used. As ion-exchanged water, water having an electric conductivity of 1 to 50 μS/cm was used. Temperature of saline solution or ion-exchanged water used for measurement was adjusted to 21° C.±2° C. before use.

In addition, when a super-absorbent resin or a diaper on the market or a super-absorbent resin in a diaper is used in a comparative test, because moisture absorption may be considered during the distribution stage, it may be subjected to drying under reduced pressure (for example, at 60 to 80° C. for about 16 hours), as appropriate, to equilibrium amount of volatile component (around 5% by weight, and 2 to 8% by weight) of a super-absorbent resin before subjecting to the comparative test.

(a) Absorption Capacity without Load to Saline Solution (an Aqueous Solution of Sodium Chloride of 0.90% by Weight) (CRCs)

Into a bag (60 mm×85 mm) made of non-woven fabric (Heatron Paper: Grade GS-22, produced from Nangoku Pulp Industry. Co., Ltd.), 0.200 g of a super-absorbent resin was uniformly charged and the bag was sealed. Then 1 L of saline solution adjusted at 21° C.±2° C. was charged into a polypropylene container (a diameter of 85 mm and a height of 200 mm) equipped with a stirrer with a length of 5 cm (a cylinder type stirrer with a length of 50 mm and a diameter of 8 mm, made of Teflon™). Then this bag made of non-woven fabric, with a super-absorbent resin charged in, was immersed into the container while stirring at 100 rpm. After 4 hours, the bag was pulled up and subjected to drainage using a centrifugal separator (Type H-122 compact type centrifugal separator produced from KOKUSAN Co., Ltd.) at 250 G (250×9.81 $m/s^2$) for 3 minutes, to measure a bag weight, $W_2$ (g). In addition, the same procedure was carried out without using a super-absorbent resin, to measure a bag weight, $W_1$ (g). Then, using these weights, $W_1$ and $W_2$, absorption capacity (g/g) was calculated by the following equation:

Absorption capacity without load to saline solution (g/g)=(Weight $W_2$(g)−Weight $W_1$(g))/(Weight of a super-absorbent resin(g))−1

(b) Absorption Capacity without Load to Ion-Exchanged Water (CRCw)

Into a bag (60 mm×85 mm) made of non-woven fabric (Heatron Paper: Grade GS-22, produced from Nangoku Pulp Industry. Co., Ltd.), 0.050 g of a super-absorbent resin was uniformly charged and the bag was sealed. Then 1 L of ion-exchanged water adjusted at 21° C.±2° C. was charged into a polypropylene container (a diameter of 85 mm and a height of 200 mm) equipped with a stirrer with a length of 5 cm (a cylinder type stirrer with a length of 50 mm and a diameter of 8 mm, made of Teflon™). Then this bag made of non-woven fabric, with a super-absorbent resin charged in, was immersed into the container while stirring at 100 rpm. After 4 hours, the bag was pulled up and subjected to drainage using a centrifugal separator (Type H-122 compact type centrifugal separator produced from KOKUSAN Co., Ltd.) at 250 G (250×9.81 $m/s^2$) for 3 minutes, to measure a bag weight, $W_4$ (g). In addition, the same procedure was carried out without using a super-absorbent resin to measure a bag weight, $W_3$ (g). Then, using these weights, $W_3$ and $W_4$, absorption capacity (g/g) was calculated by the following equation:

Absorption capacity without load to ion-exchanged water (g/g)=(Weight $W_4$(g)−Weight $W_3$(g))/(Weight of a super-absorbent resin(g))−1

(c) Amount of Volatile Component

On an aluminum dish with known weight (weight $W_5$ (g)) and a diameter of 60 mm, 2.000 g of a super-absorbent resin was uniformly dispersed and stood still for 3 hours, in a calm dryer (EYELA natural oven NDO-450 produced from Tokyo Rikakiki Co., Ltd.) heated at 180° C. After 3 hours, the aluminum dish was taken out, and gradually cooled in a desiccator for 20 minutes, to measure a weight ($W_6$ (g)). Amount of volatile component was calculated by the following equation:

Amount of volatile component (% by weight)=100×
{($W_5$[g]+2.000[g])−$W_6$[g]}/2.000 [g]

(d) Solubility Test to Ion-Exchanged Water for 30 Minutes

Into a 1 L polypropylene container (a diameter of 85 mm and a height of 200 mm), 500 mL of ion-exchanged water was charged and stirred at 400 rpm with a 5 cm stirrer (a cylinder type stirrer with a length of 50 mm and a diameter of 8 mm, made of Teflon™) and 0.500 g of a super-absorbent resin was charged therein. Time till dissolution by visual check (dissolution time by visual check) was measured. In this case, the charging time was regarded as a starting (zero) time. After 30 minutes, all of the content was poured on a 150 μm wire mesh made of stainless steel (wire mesh with mesh opening size of 150 μm, and frame dimension: a diameter of 200 mm and a depth of 45 mm, specified by JIS-Z-8801, produced by The IIDA TESTING SIEVE), and all of the solution passed through the wire mesh in 2 minutes was recovered to determine a weight ($W_7$ (g)).

Into a 500 mL round bottom flask, 200 g ($W_8$ (g)) of the solution to be recovered was weighed, and concentrated to about 5 mL by a rotary evaporator. When the amount of the solution passing the wire mesh was less than 200 g, total passing amount was used as $W_8$ (g).

The resultant concentrate was transferred into an aluminum dish with known weight (weight $W_9$ (g)) and a diameter of 60 mm, and further residue inside the flask was transferred using 5 mL of ion-exchanged water. This washing operation was repeated three times.

The aluminum dish was stood still for 3 to 5 hours until constant weight was obtained, in a calm dryer (EYELA natural oven NDO-450 produced from Tokyo Rikakiki Co., Ltd.) heated at 180° C. After that, the aluminum dish left standing to cool in a desiccator, and weight of the aluminum dish was measured ($W_{10}$ (g)).

Separately, the procedure (c) was carried out, and solid content was determined from amount of volatile component.

Solubility for 30 minutes was calculated by the following calculation equations:

Solid content (% by weight)=100 (% by weight)−
 amount of volatile component (% by weight)

Substantial sample mass (g)=(weight of sample
 used)×(solid content)×(% by weight)/100

Solubility for 30 minutes (%)=($W_{10}$[g]−$W_9$[g])×
 ($W_7$[g]/$W_8$[g])×100/(substantial sample mass [g])

(e) Mass (Weight) Average Particle Diameter (D50), Logarithmic Standard Deviation (σζ) and % by Weight of Particles with a Diameter of Smaller than 150 μm A super-absorbent resin was classified using standard JIS sieves with, for example, mess sizes of 850 μm, 710 μm, 600 μm, 500 μm, 425 μm, 300 μm, 212 μm, 150 μm, 106 μm, and 45 μm, to measure % by weight of particles having a diameter of smaller than 150 μm, and also residual %, R, of each particle size was plotted in logarithmic probability paper. By these procedures, particle diameter corresponding to R=50% by weight was determined as mass average particle diameter (D50). In addition, logarithmic standard deviation (σζ) was expressed by the following equation, wherein smaller σζ value represents narrower particle size distribution:

σζ=0.5×$ln(X_2/X_1)$ wherein $X_1$ and $X_2$ represent particle diameter for R=84.1% by weight and R=15.9% by weight, respectively.

In this connection, classification by sieves was carried out by charging 10.00 g of a super-absorbent resin on JIS standard sieves with the above mesh openings (The IIDA TESTING SIEVE: inner diameter=80 mm), and then subjecting to classification for 5 minutes by a Low Tap type sieving vibrator (ES-65 type, produced from IIDA SEISAKUSHO Co., Ltd.).

In addition, when more than half of the particles of a super-absorbent resin used for measurement is out of the range of the sieves (for example, over 850 μm or pass 45 μm), mesh openings may be changed, as appropriate.

In addition, mass average particle diameter (D50) is defined as particle diameter of a standard sieve corresponding to 50% by weight of total particles classified by standard sieves having specified mesh openings as described in U.S. Pat. No. 5,051,259, and the like.

(f) pH pH is determined by400.1-99 specified in EDANA (European Disposable And Nonwoven Association).

Specifically, 100 mL of an 0.9% by weight sodium chloride aqueous solution and a stirrer is placed in a 250 mL beaker. The solution is stirred at a suitable rate so as to prevent air from incorporating there into. Into the solution, 0.5±0.01 g of a super-absorbent resin is placed and stirred for 10 minutes. After 10 minutes, the stirring is stopped and the solution is left standing for one minute. Then, a pH electrode is put into the solution and a pH value of a supernatant is measured.

(g) Absorption Test of Absorbing Core

On a water dispersible sanitary paper with width of 5.5 cm and length of 11 cm (produced by Kawamura Seishi Co., Ltd. under product name of Swan), 0.5 g of a super-absorbent resin is uniformly scattered, and another sanitary paper is further placed thereon, to prepare a sandwich-type absorbing core. On the absorbing core, a plate (weight: 72 g) is set as a device for introducing a solution, which is a acrylic plate with width of 7 cm and length of 15 cm and into the center of which a pipe with diameter of 1.5 cm is inserted. 3.0 g of saline solution is introduced to the absorbing core through the pipe. After 10 minutes, the device for introducing a solution is removed. 4 pieces of paper towels (produced by Nippon Paper Crecia Co., Ltd. under product name of Kim Towel Wiper) with known weight (weight $W_{11}$ (g)) are placed in piles so as to cover the absorbing core. Further, a acrylic plate with width of 7 cm and length of 15 cm (weight: 70 g) and a load (weight: 460 g) are sequentially placed thereon. After 30 seconds, the acrylic plate and load are removed and a weight of the paper towels is determined ($W_{12}$ (g)). A return Rewet and a ratio of Rewet amount to amount of solution introduced are calculated by the following equations:

Rewet amount [g]=$W_{12}$[g]−$W_{11}$[g]

Ratio of Rewet amount to amount of solution introduced [%]=100×Rewet amount [g]/3.0[g]

(h) Blockage Test in Simulated Drainage Pipe

A device is used as a simulated drainage pipe device, which is a silicon tube with inner diameter of 1.2 cm and outer diameter of 1.6 cm and equipped with a funnel on one side as shown in FIG. 1. By using this device, a blockage of pipe is evaluated when an absorbing core is flown there into.

Specifically, the simulated drainage pipe device consists of a funnel part having inner diameter of 14 cm at "A" position and height from "A" position to "B" position of 12 cm, and a silicon tube part connecting "B" position with "C" position (length of 100 cm, inner diameter of 1.2 cm, outer diameter of 1.6 cm). In this case, "B" and "C" positions are fixed so as to have the height thereof identical. A distance between the center of the tube at "B" position and the center of the tube at "C" position is set to be 25 cm.

Into a 600 mL polypropylene container (a diameter of 85 mm and a height of 200 mm), a 5 cm stirrer (a cylinder type stirrer with a length of 50 mm and a diameter of 8 mm, made of Teflon™) and 100 mL of ion-exchanged water was charged therein. The absorbing core after the absorption test (g) has been completed is placed there into, and stirred at 1200 rpm for 5 seconds. Immediately thereafter, the stirrer is removed, and a dispersion of absorbing core is introduced from "A" position of the simulated pipe device, and left standing for 60 minutes. After 60 minutes, 500 mL of ion-exchanged water is poured from the funnel at "A" position, to observe how the dispersion is discharged from "C" position.

Example 1

A reaction solution was prepared by dissolving 51 g of acrylic acid (AA), 9 g of lauryl acrylate (LA) (purchased from Aldrich Chemical Co., Ltd.), 90 g of ethanol and 0.2 g of 2,2'-azobisisobutyronitrile. The reaction solution was charged into a 500 mL separable flask equipped with stirring blades, a motor for driving the stirring blades and a condenser tube, and then dissolved oxygen was purged by blowing nitrogen gas for 30 minutes. Then, under nitrogen gas flow, the separable flask was immersed in a hot bath at 60° C. and polymerization reaction was carried out for 2 hours while stirring. Then, the water bath temperature was raised to 80° C. to carry out a polymerization reaction for further 1 hour, to yield a transparent and viscous solution. The resultant solution was dried under vacuum at 60° C. for 16 hours. The resultant white lump was pulverized and passed through an 850 µm mesh screen, to yield a precursor resin (A). Mass average particle diameter of the precursor resin (A) was 415 µm and logarithmic standard deviation was 0.47.

100 parts of the precursor resin (A) and 49.6 parts of sodium hydrogen carbonate (amount corresponding to neutralize 50% by mole of acrylic acid) were mixed, and 400 parts of water was added thereto while stirring, and stood still for 20 hours. Then, after subjecting to vacuum drying at 60° C. for 16 hours, and subsequently to pulverizing, particles passing through 850 µm mesh screen but not passing 150 µm mesh screen were separated out, to yield a super-absorbent resin (1). Mass average particle diameter of the resultant super-absorbent resin (1) was 410 µm, logarithmic standard deviation was 0.45 and amount of volatile component was 4% by weight. The composition and water-absorbing performance of the super-absorbent resin (1), and test results of absorbing core using the same are shown in Tables 1, 2, and 3, respectively.

Example 2

A precursor resin (B) was obtained by following a procedure of Example 1, except that a reaction solution was prepared by dissolving 48 g of acrylic acid, 12 g of lauryl acrylate (purchased from Aldrich Chemical Co., Ltd.), 90 g of ethanol and 0.2 g of 2,2'-azobisisobutyronitrile. Mass average particle diameter of the precursor resin (B) was 420 µm and logarithmic standard deviation was 0.45.

100 parts of the precursor resin (B) and 70 parts of sodium hydrogen carbonate (amount corresponding to neutralize 75% by mole of acrylic acid) were mixed, and 400 parts of water was added thereto while stirring, and stood still for 20 hours. Then, after subjecting to vacuum drying at 60° C. for 16 hours, and subsequent pulverizing, particles passing 850 µm mesh screen but not passing 150 µm mesh screen were separated out, to obtain a super-absorbent resin (2). Mass average particle diameter of the resultant super-absorbent resin (2) was 417 µm, logarithmic standard deviation was 0.43 and amount of volatile component was 5% by weight. The composition and water-absorbing performance of the super-absorbent resin (2), and test results of absorbing core using the same are shown in Tables 1, 2, and 3, respectively.

Example 3

A precursor resin (C) was obtained by following a procedure of Example 1, except that a reaction solution was prepared by dissolving 54 g of acrylic acid, 6 g of stearyl acrylate (purchased from Wako Pure Chemical Industries, Ltd.), 90 g of ethanol and 0.2 g of 2,2'-azobisisobutyronitrile. Mass average particle diameter of the precursor resin (C) was 404 µm and logarithmic standard deviation was 0.46.

100 parts of the precursor resin (C) and 52.5 parts of sodium hydrogen carbonate (amount corresponding to neutralize 50% by mole of acrylic acid) were mixed, and 400 parts of water was added thereto while stirring, and stood still for 20 hours. Then, after subjecting to vacuum drying at 60° C. for 16 hours, and subsequent pulverizing, particles passing 850 µm mesh screen but not passing 150 µm mesh screen were separated out, to obtain a super-absorbent resin (3). Mass average particle diameter of the resultant super-absorbent resin (3) was 423 µm, logarithmic standard deviation was 0.41 and amount of volatile component was 4% by weight. The composition and water-absorbing performance of the super-absorbent resin (3), and test results of absorbing core using the same are shown in Tables 1, 2, and 3, respectively.

Example 4

A precursor resin (D) was obtained by following a procedure of Example 1, except that a reaction solution was prepared by dissolving 52.5 g of acrylic acid, 7.5 g of stearyl acrylate (purchased from Wako Pure Chemical Industries, Ltd.), 90 g of ethanol and 0.2 g of 2,2'-azobisisobutyronitrile. Mass average particle diameter of the precursor resin (D) was 429 µm and logarithmic standard deviation was 0.42.

100 parts of the precursor resin (D) and 76.6 parts of sodium hydrogen carbonate (amount corresponding to neutralize 75% by mole of acrylic acid) were mixed, and 400 parts of water was added thereto while stirring, and stood still for 20 hours. Then, after subjecting to vacuum drying at 60° C. for 16 hours, and subsequent pulverizing, particles passing 850 µm mesh screen but not passing 150 µm mesh screen were separated out, to obtain a super-absorbent resin (4). Mass average particle diameter of the resultant super-absorbent resin (4) was 436 µm, logarithmic standard deviation was 0.49 and amount of volatile component was 4% by weight. The composition and water-absorbing performance of the super-absorbent resin (4), and test results of absorbing core using the same are shown in Tables 1, 2, and 3, respectively.

Example 5

A precursor resin (E) was obtained by following a procedure of Example 1, except that a reaction solution was prepared by charging and dissolving 51 g of acrylic acid, 9 g of stearyl acrylate (purchased from Wako Pure Chemical Industries, Ltd.), 90 g of ethanol and 0.2 g of 2,2'-azobisisobutyronitrile. Mass average particle diameter of the precursor resin (E) was 419 µm and logarithmic standard deviation was 0.45.

100 parts of the precursor resin (E) and 74.4 parts of sodium hydrogen carbonate (amount corresponding to neutralize 75% by mole of acrylic acid) were mixed, and 400 parts of water was added thereto while stirring, and stood still for 20 hours. Then, after subjecting to vacuum drying at 60° C. for 16 hours, and subsequent pulverizing, particles passing 850 μm mesh screen but not passing 150 μm mesh screen were separated out, to obtain a super-absorbent resin (5). Mass average particle diameter of the resultant super-absorbent resin (5) was 413 μm, logarithmic standard deviation was 0.46 and amount of volatile component was 6% by weight. The composition and water-absorbing performance of the super-absorbent resin (5), and test results of absorbing core using the same are shown in Tables 1, 2, and 3, respectively.

Example 6

A mixed solution of 0.05 part of ethylene glycol diglycidyl ether (Nagase Kasei Co., Ltd. under product name of Deconal EX-810), 1 part of propylene glycol, 3 part of water, and 1 part of isopropyl alcohol was added by spraying while stirring to 100 parts of the super-absorbent resin (3) which was produced by Example 3, and then heated in a drier at 140° C. Subsequently, particles passing 850 μm mesh screen but not passing 150 μm mesh screen were separated out, to obtain a super-absorbent resin (6). Mass average particle diameter of the resultant super-absorbent resin (6) was 430 μm, logarithmic standard deviation was 0.42 and amount of volatile component was 2% by weight. The composition and water-absorbing performance of the super-absorbent resin (6), and test results of absorbing core using the same are shown in Tables 1, 2, and 3, respectively.

Comparative Example 1

Into 5500 g of an aqueous solution of sodium acrylate (a monomer concentration of 38% by weight) having neutralization ratio of 75% by mole, 6.25 g of polyethylene glycol diacrylate (average number of addition moles of ethylene oxide of 9) was added to obtain a reaction solution. Then the reaction solution was supplied into a 10 L stainless steel double arm-type jacketed kneader equipped with 2 sigma-type blades and a lid, and inside the system was purged with nitrogen gas while maintaining the reaction solution at 30° C. Subsequently, 29.8 g of an aqueous solution of sodium persulfate of 10% by weight and 1.5 g of an aqueous solution of L-ascorbic acid of 1% by weight were added while stirring of the reaction solution. Polymerization was initiated after about 1 minute and a polymerization peak temperature of 86° C. was observed 17 minutes after initiation of polymerization. A hydrogel-like polymer was taken out at 60 minutes after initiation of polymerization. The resultant hydrogel-like polymer was in a crushed state into about 1 to 4 mm particles. This crushed hydrogel-like polymer was spread on a 50 mesh wire net (a mesh opening of 300 μm) and dried with hot air at 160° C. for 60 minutes. Then, the dried substance was pulverized with a roll mill, and particles passing 850 μm mesh screen but not passing 150 μm mesh screen were separated out, to obtain a comparative super-absorbent resin (1). Mass average particle diameter of the resultant comparative super-absorbent resin (1) was 407 μm, logarithmic standard deviation was 0.43 and amount of volatile component was 7% by weight. The composition and water-absorbing performance of the comparative super-absorbent resin (1), and test results of absorbing core using the same are shown in Tables 1, 2, and 3, respectively.

Comparative Example 2

A comparative super-absorbent resin (2) was obtained by following a procedure of Example 5, except that 24.8 g of sodium hydrogen carbonate (amount corresponding to 25% by mole of acrylic acid) was added to a polymer. Mass average particle diameter of the resultant comparative super-absorbent resin (2) was 436 μm, logarithmic standard deviation was 0.45 and amount of volatile component was 5% by weight. The composition and water-absorbing performance of the comparative super-absorbent resin (2), and test results of absorbing core using the same are shown in Tables 1, 2, and 3, respectively.

Comparative Example 3

Into a 1 L polypropylene container, 1.05 g of lauryl methacrylate, 12.5 g of an 30% aqueous solution of sodium lauryl sulfate, 270 g of water, 36.0 g of acrylic acid, 0.024 g of 2,2'-azobisisobutyronitrile and 1 g of a polyethylene glycol-based surfactant (Emulgen 108) was dissolved, and then dissolved oxygen was purged by blowing nitrogen gas for 30 minutes. Then, under nitrogen gas flow, the container was immersed in a hot bath at 60° C. and a polymerization reaction was carried out for 4 hours.

After 4 hours, the content was cooled to room temperature and the resultant gel was pulverized with a pair of scissors. Then, 23 g of an aqueous solution of ammonium of 28% by weight was uniformly added and mixed to the pulverized gel.

After 3 hours of standing still, the gel was dried at 120° C. for 2.5 hours, and then subjected to vacuum drying at 60° C. for 16 hours, to obtain a comparative super-absorbent resin (3). The resultant comparative super-absorbent resin (3) had a mass average particle diameter of 421 μm, a logarithmic standard deviation of 0.43 and amount of volatile component of 5% by weight. The composition and water-absorbing performance of the comparative super-absorbent resin (3), and test results of absorbing core using the same are shown in Tables 1, 2, and 3, respectively.

Comparative Example 4

A reaction solution was prepared by dissolving 65 g of acrylic acid and 10 g of lauryl acrylate (purchased from Aldrich Chemical Co., Ltd.), 25 g of ethyl acrylate (EA), 106 g of acetone, 38 g of distilled water. The reaction solution was charged into a 500 mL separable flask equipped with stirring blades, a motor for driving the stirring blades and a condenser tube, and then dissolved oxygen was purged by blowing nitrogen gas for 30 minutes. Then, an aqueous solution obtained by dissolving 0.88 g of 2,2'-azobis(2-amidinopropane) dihydrochloride into 5 g of distilled water was added, and under nitrogen gas flow, the separable flask was immersed in a water bath at 70° C. and a polymerization reaction was carried out for 6 hours while stirring. After the reaction solution was cooled to room temperature, 10.5 g of a 48% by weight aqueous solution of sodium hydroxide (amount corresponding to neutralize 14% by mole of acrylic acid) and 380 g of distilled water were added for neutralization. The neutralized substance was dried under vacuum at 60° C. for 16 hours and pulverized, and by separating out particles passing 850 μm mesh screen but not passing 150 μm mesh screen, a comparative super-absorbent resin (4) was yielded. Mass average particle diameter of the resultant comparative super-absorbent resin (4) was 411 μm, logarithmic standard deviation was 0.47 and amount of volatile component was 5% by weight. The composition and water-absorbing performance of the comparative super-absorbent resin (4), and test results of absorbing core using the same are shown in Tables 1 and 2, respectively.

Comparative Example 5

A monomer solution was prepared by dissolving 43.3 g of acrylic acid, 10.7 g of AMPS (2-acrylamide-2-methylpropane sulfonic acid), 35.2 g of butyl acrylate (BA), 20 g of 2-ethylhexyl acrylate (2-EHA) into 55 g of acetone/water (70/30) mixed solution, and then by purging dissolved oxygen by blowing nitrogen gas for 30 minutes. Separately, 0.51 g of a polymerization initiator, 2,2'-azobisisobutyronitrile, was dissolved into 20 ml of acetone, and then by purging dissolved oxygen by blowing nitrogen gas for 30 minutes, an initiator solution was prepared. Into a 1000 mL separable flask equipped with 2 dropping funnels, stirring blades, a motor for driving the stirring blades and a condenser tube, 120 g of the acetone/water (70/30) mixed solution was charged, and further, dissolved oxygen was purged by blowing nitrogen gas. Then the reaction container was immersed in a water bath and heated to 60° C. and, under nitrogen gas flow, the monomer solution and the initiator solution were simultaneously and slowly dropped over 2 hours, each from the 2 dropping funnels. After completion of the dropping, the solution was subjected to polymerization reaction for further 2 hours. To the resultant polymerized substance, 4.3 g of a 48% aqueous solution of sodium hydroxide (amount corresponding to neutralize 8% by mole of acid group-containing monomer) was dropped and then subjected to vacuum drying at 60° C. for 16 hours. The resultant white lump was pulverized, and by separating out particles passing 850 μm mesh screen but not passing 150 μm mesh screen, a comparative super-absorbent resin (5) was yielded. Mass average particle diameter of the resultant comparative super-absorbent resin (5) was 407 μm, logarithmic standard deviation was 0.44 and amount of volatile component was 5% by weight. The composition and water-absorbing performance of the comparative super-absorbent resin (5), and test results of absorbing core using the same are shown in Tables 1 and 2, respectively. In the Table 1, the abbreviations are as follows acrylic acid: AA, lauryl acrylate: LA, stearyl acrylate: StA, lauryl methacrylate: LMA, 2-ethylhexyl acrylate: 2-EHA, ethyl acrylate: EA, 2-acrylamide-2-methylpropane sulfonic acid: AMPS, butyl acrylate: BA, CRCs: absorption capacity without load to saline solution CRCw: absorption capacity without load to ion-exchanged water

TABLE 1

| | Copolymerization monomer | Copolymerization ratio (wt %) | Neutralization ratio [mol % to monomer containing acid group] |
|---|---|---|---|
| Super-absorbent resin (1) | AA/LA | 85/15 | 50% |
| Super-absorbent resin (2) | AA/LA | 80/20 | 75% |
| Super-absorbent resin (3) | AA/StA | 90/10 | 50% |
| Super-absorbent resin (4) | AA/StA | 87.5/12.5 | 75% |
| Super-absorbent resin (5) | AA/StA | 85/15 | 75% |
| Super-absorbent resin (6) | Surface cross-linked super-absorbent resin (3) | | |
| Precursor resin (A) | AA/LA | 85/15 | 0% |
| Precursor resin (B) | AA/LA | 80/20 | 0% |
| Precursor resin (C) | AA/StA | 90/10 | 0% |
| Precursor resin (D) | AA/StA | 87.5/12.5 | 0% |
| Precursor resin (E) | AA/StA | 85/15 | 0% |
| Comparative super-absorbent resin (1) | Polyacrylic acid chemical cross-linked substance | — | 75% |
| Comparative super-absorbent resin (2) | AA/StA | 85/15 | 25% |
| Comparative super-absorbent resin (3) | AA/LMA | 97.3/2.7 | 76% |
| Comparative super-absorbent resin (4) | AA/EA/LA | 65/25/10 | 14% |
| Comparative super-absorbent resin (5) | AA/AMPS/BA/2-EHA | 39.7/9.8/32.2/18.3 | 8% |

TABLE 2

| | CRCs for 4 hrs [g/g] | CRCw for 4 hrs [g/g] | solubility test to ion-exchanged water for 30 min. | | pH |
|---|---|---|---|---|---|
| | | | solubility [%] | dissolution time by visual check (min) | |
| Super-absorbent resin (1) | 21.5 | 0 | 100% | within 10 min. | 5.2 |
| Super-absorbent resin (2) | 20.6 | 0 | 99% | within 10 min. | 6.0 |
| Super-absorbent resin (3) | 19.5 | 0 | 100 | within 10 min. | 5.2 |
| Super-absorbent resin (4) | 23.6 | 0 | 98% | within 10 min. | 6.0 |
| Super-absorbent resin (5) | 16.5 | 0 | 95% | within 10 min. | 6.0 |
| Super-absorbent resin (6) | 17.5 | 8 | 88% | Mostly dissolved within 10 min. | 5.2 |
| Precursor resin (A) | 1.4 | — | — | — | 2.8 |

TABLE 2-continued

|  | CRCs for 4 hrs [g/g] | CRCw for 4 hrs [g/g] | solubility test to ion-exchanged water for 30 min. | | pH |
|---|---|---|---|---|---|
|  |  |  | solubility [%] | dissolution time by visual check (min) |  |
| Precursor resin (B) | 0.9 | — | — | — | 2.8 |
| Precursor resin (C) | 2.9 | — | — | — | 2.8 |
| Precursor resin (D) | 2.1 | — | — | — | 2.8 |
| Precursor resin (E) | 1.4 | — | — | — | 2.8 |
| Comparative super-absorbent resin (1) | 41 | 440 | 10% | Large amount of undissolved residue | 6.0 |
| Comparative super-absorbent resin (2) | 5.7 | 100 | 20% | Large amount of undissolved residue | 4.4 |
| Comparative super-absorbent resin (3) | 60 | 700 | below 1% | Large amount of undissolved residue | 6.0 |
| Comparative super-absorbent resin (4) | 8 | — | — | — | 3.0 |
| Comparative super-absorbent resin (5) | 4 | — | — | — | 2.9 |

TABLE 3

|  | Return amount (g) | Ratio of Rewet amount to amount of solution introduced [%] | Blockage in pipe |
|---|---|---|---|
| Super-absorbent resin (1) | 0.2 | 7 | None |
| Super-absorbent resin (2) | 0.2 | 7 | None |
| Super-absorbent resin (3) | 0.2 | 7 | None |
| Super-absorbent resin (4) | 0.1 | 3 | None |
| Super-absorbent resin (5) | 0.3 | 10 | None |
| Super-absorbent resin (6) | 0.1 | 3 | None |
| Precursor resin (C) | 1.9 | 63 | None |
| Comparative super-absorbent resin (1) | 0.1 | 3 | Blocking |
| Comparative super-absorbent resin (2) | 1.4 | 47 | Blocking |
| Comparative super-absorbent resin (3) | 0.1 | 3 | Blocking |

It is noted from Tables 1 to 3 that the super-absorbent resin of the present invention shows high absorption capacity to saline solution (a 0.9% by weight aqueous solution of sodium chloride), along with excellent solubility in water. Accordingly, it is observed that the super-absorbent resin of the present invention can be used to design a disposable diaper or a sanitary napkin which can be flown into a flushing toilet.

INDUSTRIAL APPLICABILITY

A super-absorbent resin obtained by the present invention, because of having absorption characteristics different from conventional one, has excellent absorption performance to body fluid and use feeling similarly as in conventional one, and further effect of providing convenience that it can be flown into a flushing toilet, and the like, as it is.

The entire disclosure of Japanese Patent Application No. 2005-288437 filed on Sep. 30, 2005 including specification, claims, drawings and summary are incorporated herein by reference in its entirety.

What is claimed is:

1. A super-absorbent resin comprising a repeating unit comprising an ionic dissociation group in its main or side chain, wherein said resin has an absorption capacity without load to saline solution for 4 hours of not smaller than 10 g/g, and a solubility in ion-exchanged water of not lower than 70% by weight, wherein said super-absorbent resin is a particulate super-absorbent resin, and a mass average particle diameter of the particles is in a range of 150 to 3000 μm,
   wherein a neutralization ratio of the ionic dissociation group is in a range of 50 to 90% by mole, based on the total ionic dissociation groups, and
   wherein a logarithmic standard deviation of a particle size distribution of the particles is in a range of 0.20 to 0.60.

2. The super-absorbent resin according to claim 1, wherein the ionic dissociation group is selected from the group consisting of carboxyl group, sulfonic acid group, phosphoric acid group and a salt thereof.

3. The super-absorbent resin according to claim 2, wherein the salt is selected from the group consisting of lithium salt, sodium salt, potassium salt and ammonium salt.

4. The super-absorbent resin according to claim 1, wherein the repeating unit is (meth)acrylic acid and/or salt thereof.

5. The super-absorbent resin according to claim 1, wherein an absorption capacity without load to ion-exchanged water for 4 hours is not higher than the absorption capacity without load to saline solution.

6. The super-absorbent resin according to claim 1, wherein the super-absorbent resin further comprises a hydrocarbon group with carbon atoms of not lower than 4 at the side chain.

7. The super-absorbent resin according to claim 6, wherein a weight ratio of the repeating unit derived from a monomer having the ionic dissociation group at the side chain, and a repeating unit derived from a monomer having the hydrocarbon group with carbon atoms of not lower than 4 at the side chain, is in the range of 50:50 to 99:1, in the repeating unit of the super-absorbent resin.

8. The super-absorbent resin according to claim 1, wherein the super-absorbent resin has a pH in the range of 4.0 to 8.0.

9. An absorbing core or absorbing goods of excrement, urine or blood, comprising the super-absorbent resin according to claim 1.

10. The absorbing core or absorbing goods according to claim 9, wherein the ionic dissociation group is selected from the group consisting of carboxyl group, sulfonic acid group, phosphoric acid group and a salt thereof.

11. The absorbing core or absorbing goods according to claim 10, wherein the salt is selected from the group consisting of lithium salt, sodium salt, potassium salt and ammonium salt.

12. The absorbing core or absorbing goods according to claim 9, wherein the repeating unit is (meth)acrylic acid and/or salt thereof.

13. The absorbing core or absorbing goods according to claim 9, wherein an absorption capacity without load to ion-exchanged water for 4 hours is not higher than the absorption capacity without load to saline solution.

14. The absorbing core or absorbing goods according to claim 9, wherein the super-absorbent resin further comprises a hydrocarbon group with carbon atoms of not lower than 4 at the side chain.

15. The absorbing core or absorbing goods according to claim 9, wherein a weight ratio of the repeating unit derived from a monomer having the ionic dissociation group at the side chain, and a repeating unit derived from a monomer having the hydrocarbon group with carbon atoms of not lower than 4 at the side chain, is in the range of 50:50 to 99:1, in the repeating unit of the super-absorbent resin.

16. The absorbing core or absorbing goods according to claim 9, wherein the super-absorbent resin has a pH in the range of 4.0 to 8.0.

17. The super-absorbent resin according to claim 1, wherein a weight average molecular weight of the super-absorbent resin is in a range of 10,000 to 2,000,000.

* * * * *